STERILIZABLE AND STERILIZED HYPODERMIC SYRINGE ASSEMBLIES
Original Filed Feb. 26, 1958 4 Sheets-Sheet 1
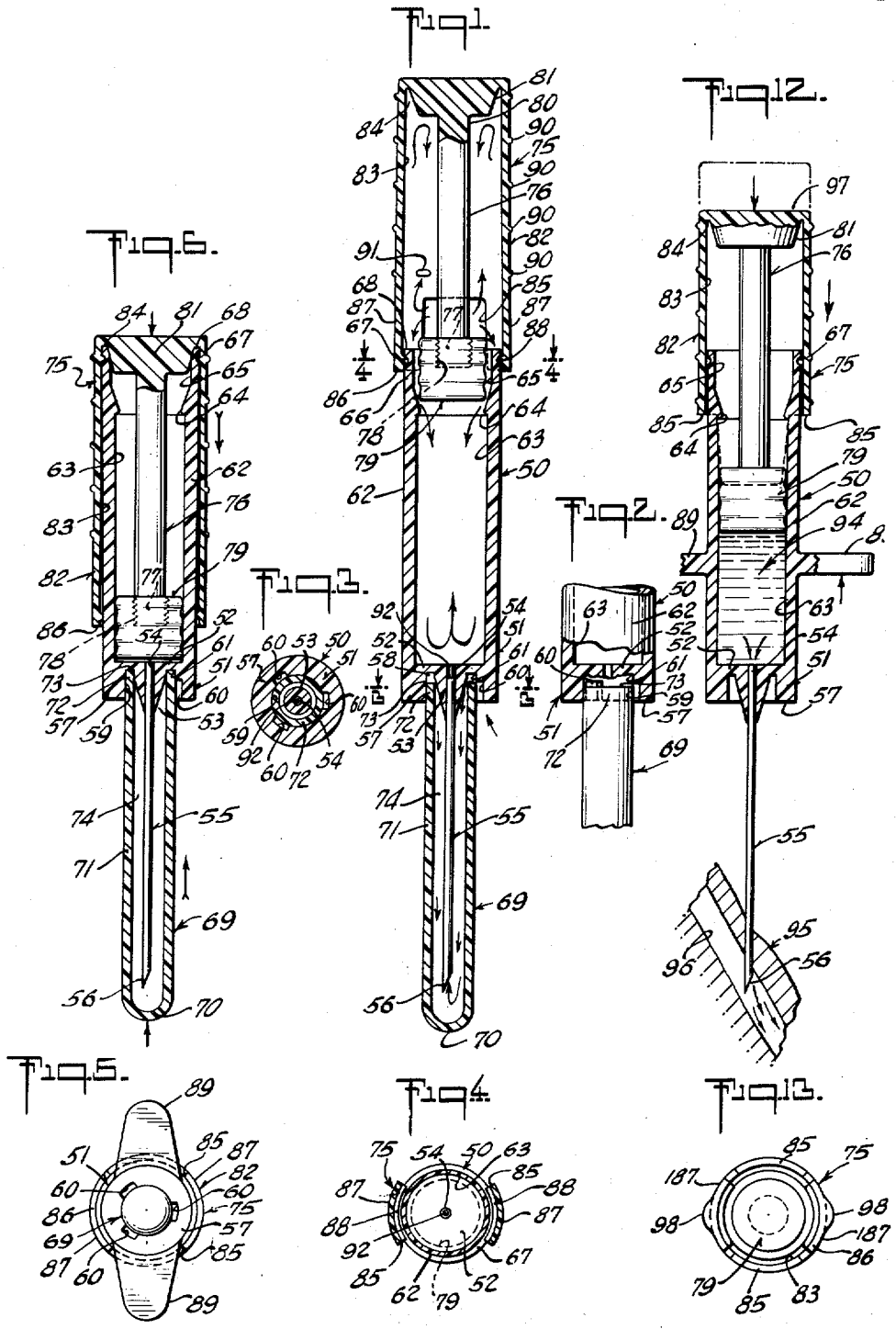

STERILIZABLE AND STERILIZED HYPODERMIC SYRINGE ASSEMBLIES

Original Filed Feb. 26, 1958 4 Sheets-Sheet 2

STERILIZABLE AND STERILIZED HYPODERMIC SYRINGE ASSEMBLIES

Original Filed Feb. 26, 1958 4 Sheets-Sheet 3

STERILIZABLE AND STERILIZED HYPODERMIC SYRINGE ASSEMBLIES
Original Filed Feb. 26, 1958 4 Sheets-Sheet 4
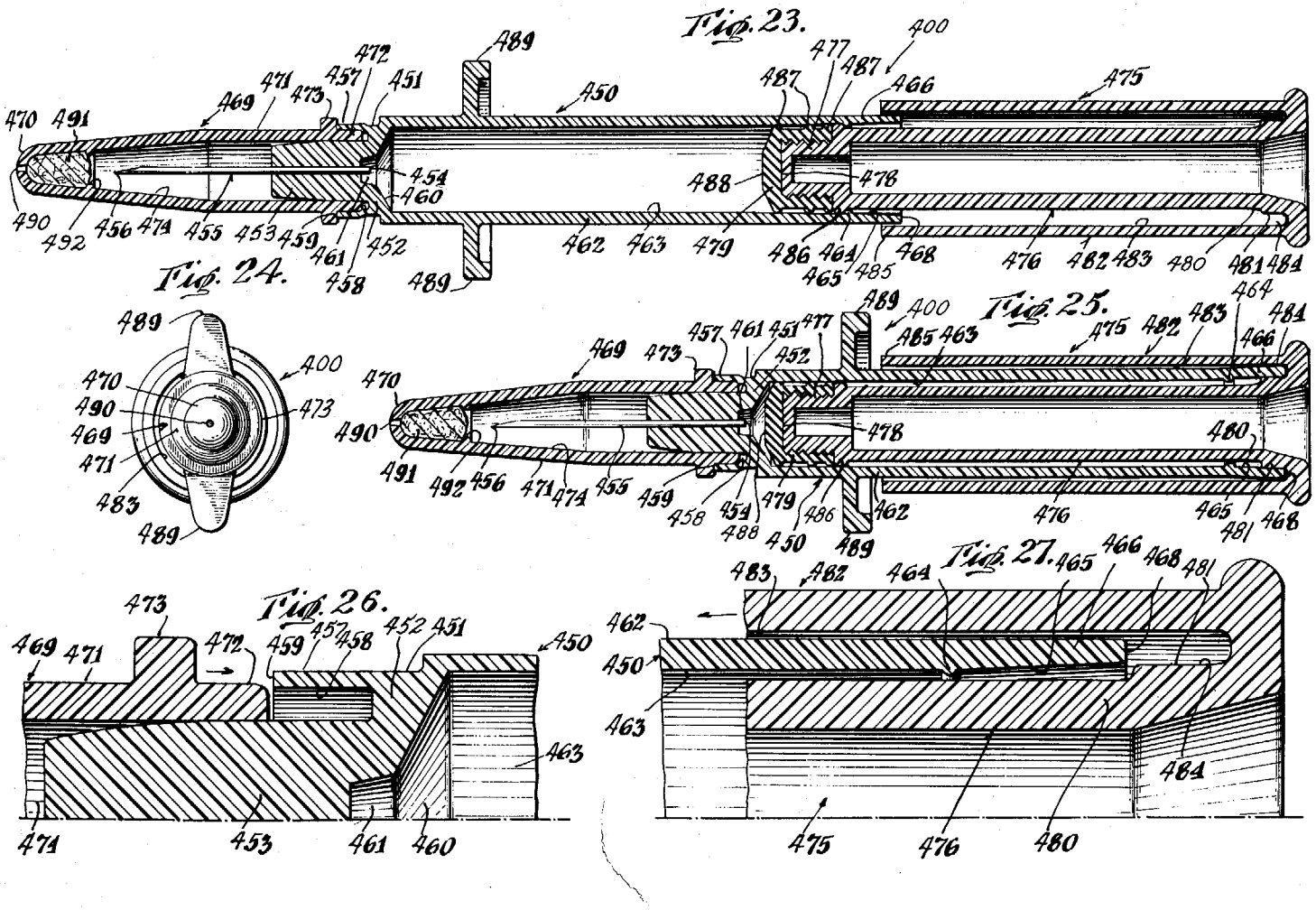

United States Patent Office

Re. 25,113
Reissued Jan. 9, 1962

25,113

STERILIZABLE AND STERILIZED HYPODERMIC SYRINGE ASSEMBLIES

Edgar H. Wilburn, Rutherford, N.J., assignor to Johnson & Johnson, New Brunswick, N.J., a corporation of New Jersey Original No. 2,860,635, dated Nov. 18, 1958, Ser. No. 720,804, Feb. 26, 1958. Application for reissue Oct. 31, 1960, Ser. No. 66,381
23 Claims. (Cl. 128—218)

Matter enclosed in heavy brackets [ ] appears in the original patent but forms no part of this reissue specification; matter printed in italics indicates the additions made by reissue.

The present invention relates to hypodermic syringe devices for injecting parenteral liquid medicaments and, more particularly, to the types intended to be loaded by the operators just prior to injective use although not limited to the latter; and the present application is in part a continuation of my pending applications Serial No. 520,409 filed July 7, 1955, and Serial No. 647,312 filed March 20, 1957, now abandoned.

A general object of the present invention is to provide such devices wherein the parts may be readily manipulated or assembled together in relative positions permitting thorough sterilization of all parts intended to contact parenteral liquids with which they are to be loaded for injective use in the patient's body, and so that internally they or parts thereof will after such sterilization be protectively isolated from airborne bacteria or closed off in a manner for efficient maintenance of such sterilized condition through subsequent handling preceding loading, such as that which may attend storage and distribution to the ultimate users.

A more specific object of the invention is to provide in such syringe assemblies protective closure means associated with chamber-providing barrel structure which under one condition provides thereat an open sterilizing fluid flow passage leading from the surrounding atmosphere directly to the space within such cap means for flow through to and from the latter of sterilizing fluid or gaseous medium, heated if desired, to or from the liquid housing chamber of the barrel structure and which under another condition effectively blocks flow through such passage of airborne bacteria for maintaining efficiently a sterilized condition while permitting simple conditioning for loading and then injective use.

Another object of the present invention is to provide in such assemblies manipulatable back end opening and closing or valving means of a protective nature to employ with isolating head cap means, whereby flow of sterilizing fluid through the entire assemblies and about their internal parts may be readily permitted in an efficient cleansing manner, and which thereafter will allow in a simple manner efficient closing off of the back end and isolating of the head end from airborne bacteria to retain the sterilized condition of the interiors and internal parts thereof.

A further object of the present invention is to provide such syringe assemblies in forms whereby injective needle means thereof are subjected to such sterilizing flow of cleansing fluid and then securely isolated in housing structures of the assemblies effectively to maintain their sterile condition until injective use.

Still another object of the invention is to provide such assemblies in a form in which means securely closes off or houses syringe front end structure which may include injective needle means, and means effectively closes off the back end of barrel structure with, if desired, piston means housed in the latter, such closed construction and means thereof effectively maintaining until manipulation for hypodermic use sterile condition of the interior of the assembly and parts thereof which may have been attained by heat radiation and/or conduction after the parts were brought together in a manner to form the closed assembly.

A still further object of the invention is to provide such a hypodermic syringe device featuring injective needle means permanently carried by the front end of barrel structure with the latter fitted with parenteral liquid-expelling piston means, the injective needle means being effectively covered by removable cap means efficiently isolating it from airborne bacteria with the piston means providing valving and protective hood means together permitting ready and effective internal sterilization and maintenance of internal sterile conditions until loaded for injective use.

Another object of the present invention is to provide in such assemblies manipulative piston means each of which includes hood structure which provides at the back end of the barrel structure a valving device which in a retracted position is in valve open position to permit ready through flow of sterilizing fluid while remaining protectively telescoped with the barrel structure, the forward position of the piston means providing closure of the valve means under conditions of balanced pressures prevailing inside and outside of the assembly while allowing automatic valving under conditions of unbalanced pressures.

An additional object of the invention is to provide such a hypodermic syringe assembly in which the front end protective cap means has a relatively small, permanently open passage provided with suitable filtering means assuring internal isolation from bacteria in the surrounding atmosphere when in mounted needle-covering position.

A still further object of the present invention is the provision of a structural embodiment of the device which is readily and economically constructed on a mass production basis and which while permitting efficient sterilization and operation thereof allows discard after a single injective use.

Other objects of the invention will in part be obvious and will in part appear hereinafter.

The invention accordingly comprises the features of construction, combinations of elements, and arrangement of parts, which will be exemplified in the constructions hereinafter set forth, and the scope of the invention will be indicated in the claims.

For a fuller understanding of the nature and objects of the invention, reference should be had to the following detailed description taken in connection with the accompanying drawings, in which:

FIG. 1 is a axial section of an embodiment of the hypodermic syringe of the present invention, illustrating relative initial positions of parts which will permit passage therethrough of sterilizing gaseous medium;

FIG. 2 is an elevational detail, with parts broken away and in section, of the head end of the barrel and associated back end of the head end protective cap structure of the FIG. 1 embodiment;

FIG. 3 is a transverse section taken substantially on line 3—3 of FIG. 1;

FIG. 4 is a transverse section taken substantially on line 4—4 of FIG. 1;

FIG. 5 is an end elevational view of the structure shown in FIG. 1 as viewed from the capped head end thereof;

FIG. 6 is an axial section of the embodiment illustrated in FIGS. 1 to 5 incl., showing the relative positions of parts after they have been sterilized and then telescoped together to close off passages which were provided for passage of sterilizing gases with the parts in the relative positions shown in FIG. 1;

FIG. 12 is an axial section of the embodiment of the hypodermic syringe structure shown in FIGS. 1 to 11 incl., illustrating piston ejection of parenteral liquid contents into a person's vein;

FIG. 13 is a front end elevational view of piston structure similar to that of the embodiment illustrated in FIGS. 1 to 12 incl., proposing certain strengthening of flexible arms of the cap means thereof;

FIG. 23 is an axial section of a preferred embodiment of the hypodermic syringe assembly of the present invention, illustrating relative positions of the parts thereof when the piston or plunger means is retracted to its rearward or "stop" position;

FIG. 24 is a front end view of the hypodermic syringe device shown in FIG. 23;

FIG. 25 is an axial section of the structure shown in FIGS. 23 and 24, illustrating relative positions of parts thereof when the piston or plunger means is thrust forward fully to its forward position;

Figure 7:
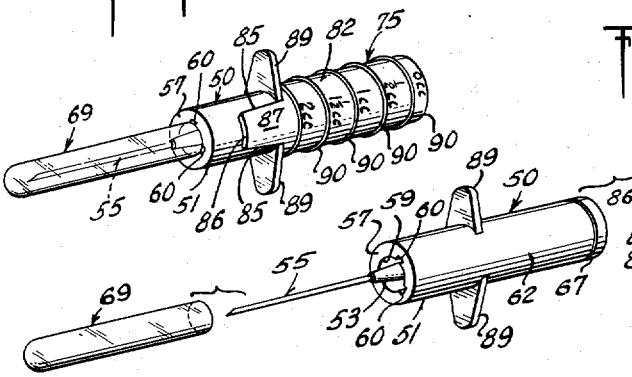
FIG. 7 is a perspective view to a smaller scale of the structure shown in FIG. 6 and with the parts in the same relative positions.

FIG. 26 is an enlarged sectional detail of the proximal or head end of the barrel structure and the distal or back end of the needle protective cap of the device illustrated in FIGS. 23–25, shown prior to telescopic interfitting mount of the latter to the former; and FIG. 27 is an enlarged sectional detail of the distal or back end of the barrel structure and the distal or back end of the piston or plunger means of the device illustrating interfitting mount of the latter to the former.

Referring to the drawings, in which like numerals identify similar parts throughout, it will be seen that the present invention involves the provision of sterilizable hypodermic syringe assemblies of various types and forms comprising in combination syringe chamber or barrel means which has or is to be provided with means for injecting parenteral liquid medicaments, e.g., cannula means or injective needle devices, means to expel the parenteral liquid contents of the chamber or barrel means, and removable cap means which protectively houses parts thereof and isolates portions protectively from airborne bacteria in the surrounding atmosphere or air to maintain the sterile condition of parts of the syringe assemblies until such time as injective use thereof is desired. In various embodiments protective cover or closure means are provided at both ends of barrel structure to isolate the interior thereof with, if desired, suitable injective needle means housed at the front end and preferably piston means reciprocatively located in the barrel structure, the parts and interiors thereof having been effectively sterilized with the closure or isolating means assuring maintenance of the sterile condition of parts. If sterilization is to be effected without through flow of sterilizing fluid, such as by heat radiation and/or conduction, the sterilizing is accomplished after the construction or assembly is protectively closed; but if sterilization is to be effected by through flow of sterilizing fluid the structure of the isolating cap means is such as to provide open sterilizing fluid flow passages or ways for effective sterilization of parts as they may be temporarily held together with such passages or ways having associated means preventing or blocking flow therethrough into the interior of the assembly, after the latter has been suitably sterilized, of airborne bacteria or air laden with bacteria. Certain embodiments employ the cap means in a manipulative form movable to passage-open position for permitting flow thereinto or therethrough of sterilizing fluid and which may then be simply manipulated to close the valved passages or ways. In some modifications a valved sterilizing-fluid passage or way is provided at the protective cap means and leads from the atmosphere exterior of the cap and barrel means directly to the space within the cap means so that sterilizing fluid may flow into and out of the latter and about the structure housed by it via the liquid outlet passage through the barrel head structure which provides the injective outlet for the parenteral liquid. The terms "passage" and "way" are used herein in the sense of one or more paths of flow since part of a flow passage or way may be provided by a single or plurality of grooves, notches, holes, and the like; and the flow of sterilizing gaseous medium therethrough may be in either direction as conditions may dictate.

In the embodiment illustrated in FIGS. 1 to 12 inclusive, barrel structure 50 may be suitably molded from any suitable material which preferably may be a plastic of a composition substantially non-contaminable of parenteral liquid to be loaded thereinto and injectively discharged therefrom. For example, barrel 50 may be molded from polyethylene which is somewhat elastic when in thin section. Barrel means 50 preferably comprises a head end structure 51, including a head cross wall 52 carrying an outwardly-projecting boss 53 through which is fixed the back end 54 of an injective cannula or needle 55 having its tip 56 sharpened for facilitating subcutaneous insertion. The barrel head end structure 51 also includes a forwardly-extending cylindrical flange 57 arranged concentric with the needle-anchoring boss 53 to provide therebetween an annular groove 58. As is illustrated in FIGS. 2 and 3, the inner cylindrical wall 59 of the circular flange 57 is provided with a plurality trated in FIGS. 23–26, shown prior to complete telescop- of longitudinally-extending notches 60—60 which extend only partially of the full depth of the groove 58 to retain a circular bottom sealing zone 61 of the cylindrical inner wall 59. The barrel structure 50 preferably has a cylindrical side wall 62 which defines a cylindrical bore 63 closed off at the front end by head structure cross wall 52 and with which the bore of cannula or needle 55 communicates. Thus, the cannula or needle bore constitutes the liquid outlet passage for the parenteral liquid chamber defined by the cylindrical side wall 62 and the head structure cross wall 52. Near the back end of the barrel structure 50 bore 63 preferably is provided with an internal constriction or circular rib 64 to serve as a plunger means or piston plug stop, as is more fully explained hereinafter. Rearwardly of the stop rib 64 the barrel bore 63 is counterbored at 65 to provide thereby a socket preferably having a diameter somewhat larger than the diameter of the bore 63 and for a purpose to be indicated later. Such counterboring 65 provides the rear zone of the barrel cylindrical wall 62 with a substantially thinner walled zone 66 which, by virtue of being thinner, is somewhat more flexible. Within the rear zone 66 of the barrel wall is provided an outside annular groove 67, preferably located near the rear edge 68 of the barrel in the form of circumambient lateral back end structure defining an open chamber back end, and which may have a plurality of functions, as explained hereinafter.

An elongated thimble-like cap means or capsule structure 69 is provided for housing front end structure, e.g. the needle 55, and preferably has a closed front end 70, a substantially cylindrical side wall 71, and a cylindrical rear end 72 which snugly fits for telescopic sliding action within the cylindrical inner wall 59 of the circular flange 57. The protective cap 69 may be molded from any suitable material, such as plastic, and may be substantially rigid when formed of more brittle plastic material, such as polystyrene, or if desired may have some elasticity if molded from a more elastic plastic material, such as polyethylene. Frictional fit retains the cylindrical rear end 72 of the cap 69 within annular flange 57 in the position illustrated in FIG. 1. In such position of cap 69 fluid or gaseous medium may flow to or from the exterior of the cap and barrel structure 50 through the passage or way provided successively by longitudinal notches 60—60, the open portion of annular groove 58 behind the back edge 73 of the rear end of the cap, the space between the boss 53 and the inner wall of the cap, the space 74 within the cap, and the bore of the needle 55. This will be considered the valve open position of the cap 69 in which the valved sterilizing-fluid passage or way at the cap rear end is open.

Plunger means 75 of the syringe assembly of FIGS. 1 to 12 inclusive may include suitable piston structure 76, preferably in the form of an elongated shaft or stem having an externally-threaded head end 77 threadably received or mounted within an internally-threaded socket 78 in the back end of a piston plug 79 which may be molded from suitable elastic-material, such as rubber or the like. Back end or root 80 of piston shaft or stem 76 preferably is made or molded integral with a plugging element 81 which may be frusto-conical in shape, as shown, and of such dimensions as to wedge into the open back end of the barrel counterbore 65 for secure and sealing closure thereof. The plugging element 81 and the piston shaft 76 preferably are housed coaxially within rear cap means 82 which may be molded integral therewith. Preferably the rear cap means 82 is elongated and provided with a substantially cylindrical bore 83 to define an elongated skirt or hood, as shown. Skirted cap means or hood 82 defines with the conical surface of the plugging element 81 a V-shaped annular groove 84 into which the rear edge 68 of the barrel may be wedged for enhancing the sealing of the rear end of the barrel chamber or bore 63. The plunger means or assembly 75 comprising piston shaft 76, plugging element 81 and rear cap means 82 may be molded integral from any suitable material, such as rigid, semi-rigid, or somewhat elastic plastic, e.g., polystyrene or polyethylene.

The side walls of the front end or skirt of the rear cap 82 preferably are provided with a fluid passage or flow way, such as one or more side openings, which may be in the form of a pair of diametrically-opposed notches 85, 85 extending from the front edge 86 longitudinally back an appreciable distance, as is best seen in FIGS. 1 and 7 to 10 inclusive. Such diametrically-opposed notches 85, 85 define therebetween a pair of diametrically-opposed legs 87, 87, each of which is provided internally near edge 86 with a circular rib segment 88 which snaps into the annular barrel groove 67 in the outward or rearward position of the plunger assembly 75.

In order to facilitate manual grasp and manipulation of the hypodermic syringe device illustrated in FIGS. 1 to 12 inclusive barrel 50 is provided with suitable finger grasps, such as a pair of diametrically-opposed, laterally-extending finger wings 89, 89 which are receivable in the diametrically-opposed notches 85, 85 of the skirt of the rear cap 82 to permit the latter to be pushed completely forward to the barrel chamber zero capacity or fully expelled position, as is best seen in FIG. 7, which incidentally is the position illustrated in FIG. 6, with the piston plug 79 substantially abutted against the head structure cross wall 52.

Figure 8:
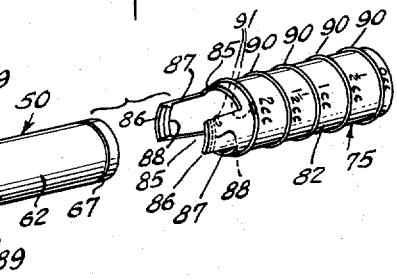
FIG. 8 is an exploded perspective view, with parts broken away and omitted, of the structure shown in FIG. 7.
Figure 11:
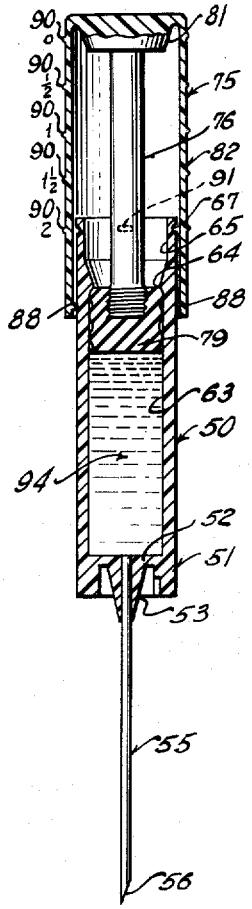
FIG. 11 is an axial section taken substantially on line 11—11 of FIG. 10, showing the syringe structure loaded with parenteral liquid and readied for hypodermic injection of contents.
Figure 10:
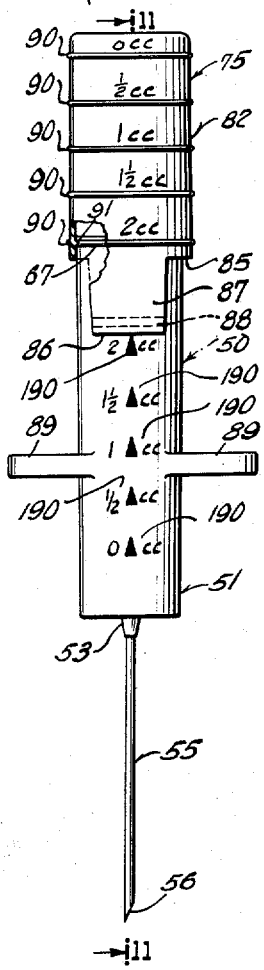
FIG. 10 is a side elevational view of the syringe structure shown in FIG. 9 but taken in a plane normal to that in which the FIG. 9 structure is viewed.

Various types of index or scale means may be provided cooperatively on the barrel 50 and the rear cap 82 to guide the amount of load or quantity of parenteral liquid drawn into the barrel bore or chamber 63 by retraction of the plunger assembly 75 and one such form is illustrated in the embodiment of FIGS. 1 to 12 inclusive, a supplemental or alternative form being indicated in FIG. 10. Such index or scale means, as there illustrated, may comprise a series of circular ribs 90—90 arranged about the exterior surface of the rear cap 82 and preferably may be formed in the molding of the latter, with each suitably identified with volume indicia, such as "0 cc.," "½ cc.," "1 cc.," "1½ cc.," and "2 cc." When one of the ribs 90 is brought to substantial alignment with the barrel groove 67 the volume of the barrel chamber 63 is substantially that of the volume mark on the rear cap 82 and this may be readily determined by observation when the rear cap is molded from transparent material, such as clear polystyrene or foggy polyethylene which in relatively thin section can be clearly seen through. In order to facilitate proper alignment of any particular cap rib 90 with barrel groove 67, the inner wall of the rear cap may be provided with a plurality of pairs of diametrically-opposed nibs 91—91, each pair being associated with one of the ribs, as indicated in FIGS. 1, 8 and 10. When any particular cap rib 90 is brought to substantial alignment with barrel groove 67, the pair of diametrically-opposed internal nibs 91, 91 on the inner wall of the cap associated with this rib and lying substantially in the same transverse plane, as shown in FIG. 10, will snap into the barrel groove by virtue of the elasticity of either the barrel material or the cap and nib material, or of both. Such index or scale ribs 90—90 may also serve to facilitate manual grip of the plunger assembly 75.

Such index or scale means comprising plunger cap ribs 90—90 and cooperating barrel groove 67 may be supplemented by other scale or index means, such as that proposed in FIG. 10, or such may be used in substitution for the other. As there indicated the scale may comprise suitable indicia or markings 190—190 imprinted on a side of the barrel 50 with which transverse free edge 86 of one of the plunger cap legs 87 is to be successively aligned as an indicator element. Such index or scale means is particularly useful if it is desired to avoid problems of molding ribs 90—90 on plunger cap 82 and/or to form the latter from opaque material.

The parts of the hypodermic syringe device illustrated in FIGS. 1 to 12 inclusive preferably will be assembled for sterilization and then subsequent packing and use in the following manner. The barrel 50 with its fixed single-ended needle 55 will have applied to the head structure 51 thereof a needle-protective cap 69 which, as will be seen from FIG. 1, will be telescoped over the needle with the edge skirt zone 72 of the cap slidably received within the cylindrical head flange 57. Such initial telescope or slidable mount of the skirt zone 72 of the needle-protective cap 69 within the barrel head flange 57 will be only to a limited degree, as illustrated in FIGS. 1 and 2, so that fluid passage is provided through the plurality of longitudinal grooves 60—60 in the inner wall of the head flange, thence into the unfilled portion of the annular groove 58 around behind and past the inner edge 73 of the cap skirt, and then between the spaced inner wall of the cap skirt zone 72 and the boss 53 to the space 74 within the needle-protective cap. This communicates the atmosphere exterior of the barrel 50 and cap 69 directly to the space 74 within the cap by a fluid passage or way at the cap. The space within the cap 69 is in communication with the barrel chamber or bore 63 by way of the needle bore 92 which constitutes the liquid outlet passage of the barrel. A suitable piston plug, such as that illustrated at 79, will be mounted on the forward end of piston stem or shaft 76, such as by threaded engagement, and the piston rear cap 82 will then be assembled to the rear end of the barrel 50 by snapping the interior rib segments 88, 88 of the rear cap legs 87, 87 into the annular barrel groove 67, as illustrated in FIG. 1. Such mounting of the plunger assembly 75 to the rear end of the barrel 50 disposes the piston plug 79 within the counterbore 65 of the barrel bore while providing space between the inner wall of the latter and the piston plug for free passage of fluid or gaseous medium, as illustrated in FIG. 1. This mounting of the piston assembly 75 to the rear end of the barrel 50 in the rearmost or fully retracted position, as illustrated in FIG. 1, leaves appreciable portions of the diametrically-opposed cap notches 85, 85 uncovered by barrel structure for free passage of fluid to and/or from the rear end of the latter.

A plurality of such hypodermic syringe assemblies, such as that illustrated in FIG. 1 are then suitably loaded into a closable sterilizing tank. After loading of the sterilizing tank it is closed and the air therein and in the open syringe assemblies exhausted therefrom with simultaneous supply to the closed tank of suitable sterilizing liquid or gaseous medium, such as formalin, ethylene oxide or steam. When gaseous mediums other than steam are employed they may be heated, if desired. As a result, the sterilizing fluid or gaseous medium not only flows completely about each of the hypodermic syringe assemblies in the tank but also through the interior of each of the syringe assemblies by way of the open valved sterilizing-fluid passage at the front needle-protective cap 69 previously described, through the barrel bore or chamber 63, about the piston plug 79 and its supporting piston stem 76, and through the plunger assembly cap notches 85, 85. For example, such sterilizing gaseous medium may flow through the longitudinal notches 60—60 in the inner wall of the barrel head flange 57 into the annular groove 58 of the barrel head structure 51, across behind the inner end 73 of the needle-protective cap 69, back between the inner wall of the needle-protective cap skirt zone 72 and the needle-anchoring boss 53 to the space 74 within the needle-protective cap. The sterilizing gaseous medium may then flow from the space 74 within the needle-protective cap 69 via the needle bore 92 into the barrel chamber or bore 63, from the latter past the constricting stop rib 64 through the clearance or space provided between the substantially cylindrical exterior surface of the piston plug 79 and the inner wall of the counterbore 65 into the space defined by the bore 83 of the plunger assembly rear cap 82, and thence through the diametrically-opposed notches 85, 85 in the skirt of the rear cap to tank atmosphere. Of course, the direction of flow of sterilizing gaseous medium may be in the reverse direction or a combination of both directions as the air in the syringe assembly of FIG. 1 is withdrawn from the sterilizing tank for replacement by the sterilizing gaseous medium.

After sterilization of the plurality of assemblies of the FIG. 1 type in the sterilizing tank, the latter is opened by the operator and the interiors of the assemblies immediately closed off by a simple procedure of pushing the piston assembly 75 of each forward to its extreme forward closing position and then pushing the needle-protective cap 69 of each back to its rearmost closing position, as illustrated in FIG. 6. It will be noted that with the needle-protective cap 69 pushed completely back so that its skirt edge zone 72 is wedged into the bottom of annular groove 58, a fluid seal is provided at the root of the boss 53 and the exterior surface of the edge of the cap is lapped by the uninterrupted cylindrical surface of the zone 61 of the interior wall 59 of projecting head flange 57. It will also be noted that the back edge 68 of the barrel is wedged into the annular groove 84 between the inner surface 83 of the piston cap wall and the frusto-conical plug 81, securely closing off the back end of the barrel chamber 63. A molded cylindrical bore has slight taper to permit withdrawal of the core and thus any barrel bore will be of slightly less diameter at the closed end then at the free edge. For example, in a working model of the present syringe the barrel bore may be about 1.375 inches long having a diameter at the head cross wall 52 of about 0.370 inch and in the vicinity of stop rib 64 be of a diameter of about 0.375 inch. Similar taper would be provided in the molding of the bore 83 of the plunger rear cap 82, and thus in the absence of the plugging element 81 at the root of the piston stem 76 secure fluid seal will be attained by wedging between the exterior surface of the back end 68 of the barrel 50 and the interior surface of the plunger cap bore adjacent the root of the piston stem. However, the wedging of the plugging element 81 into the counterbore 64 of the barrel assures a secure fluid seal thereat with a tendency for the plugging element slightly to spread the back edge 68 of the barrel and snug its exterior surface more securely against the surface of cap bore 83. The sterilized assembly of FIG. 6 is then packaged for distribution.

In use and operation of the assembly of FIG. 6, the physician or the person who is to administer an injection of parenteral liquid will withdraw the needle-protective cap 69 and discard it. He then thrusts the needle point 56 through the pierceable seal of a suitable multi-dose container, indicated in dotted lines at 93 in FIG. 9, and retracts the plunger assembly 75 to a position dictating a capacity of the syringe chamber substantially equivalent to the volume of the injection to be administered, say 2 ccs.; e.g., where the "2 cc." rib 90 becomes aligned with the barrel groove 67, and with the internal diametrically-opposed nibs 91, 91 opposite that rib snapping into that groove, or when cap leg edge 86 aligns with "2 cc." mark 190 on the side of the barrel. Suction created on the barrel chamber 63 will cause the parenteral liquid to be drawn up from the container 93 into the barrel chamber and the syringe device will thus be loaded for use, such loaded syringe assembly being illustrated in FIGS. 10 and 11 with the 2 ccs. body of parenteral liquid indicated in the latter at 94. The needle tip 56 will then be thrust into a patient's flesh, such as that indicated at 95 in FIG. 12, and if the parenteral liquid is of the intravenous type, the usual aspirating precautions for a show of blood will be taken to assure that the needle bore is in communication with a vein, such as that indicated at 96 in FIG. 12. The person administering the injection holds the barrel 50 ahead of the finger wings 89, 89 between two fingers and with this thumb applies thrust to the back end 97 of the plunger assembly cap 82 to expel the parenteral liquid 94 from the syringe chamber 63 through the needle bore 92 into the patient's vein by piston action or forward travel of the piston plug 79.

Figure 9:
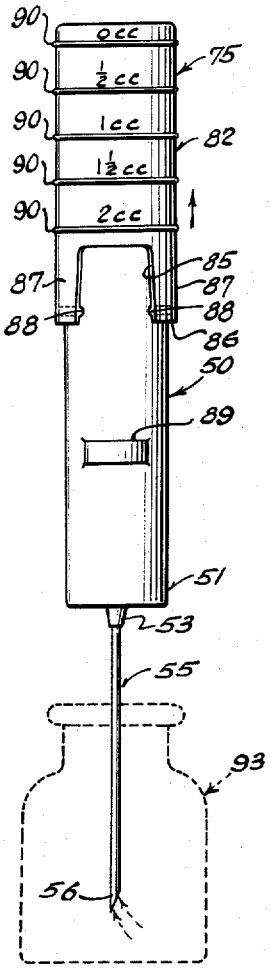
FIG. 9 is a side elevational view, illustrating manipulation of parts of the embodiment of the hypodermic syringe structure illustrated in FIGS. 1 to 8 incl. to draw into the barrel chamber a charge of parenteral liquid.

When syringe assemblies are successively loaded in such fashion from multi-dose supply containers, such as that illustrated at 93 in FIG. 9, it is a common practice to replace withdrawn parenteral liquid with atmospheric air to avoid creating a partial vacuum or low pressure conditions in the container which would tend to resist effective syringe-loading suction on the parenteral liquid contents of the supply container. This is usually done by retracting or drawing the piston back to fill the syringe chamber with atmospheric air and then after the needle is thrust through the pierceable seal or closure of the supply container thrusting the piston forward to expel the chamber air into the supply container. Thereafter, the piston is then again retracted to draw parenteral liquid into the syringe chamber; and the syringe is then injectively used in the above-indicated manner. Such practice of pumping atmospheric air into the supply container frequently causes sufficient concentration of airborne bacteria eventually to be developed in the supply containers as to cause mold growth and spoilage of parenteral liquid therein. The assemblies of the present invention may be employed in a manner to avoid any such tendency to cause spoilage and mold growth, while permitting pumping of gaseous medium such as air into the supply containers at the time syringes are to be loaded with parenteral liquid therefrom. For example, after sterilization of the FIG. 1 assembly the piston assembly may be thrust forward until its piston head means or plug 79 passes just beyond stop rib 64 to the full line position of FIG. 11, whereby the back end of the barrel bore 63 is effectively closed in a fluid-tight manner but the syringe chamber contains about 2 ccs. of sterile gaseous medium, maintained entrapped therein by subsequent thrust rearward of the needle-protective front cap 69 to the FIG 6 position. Thus the sterilized and sealed syringe assemblies of the present invention, such as the embodiment of FIGS. 1 to 12 inclusive, may be distributed to the ultimate operators either in an empty condition, wherein the closed barrel chamber has practically no fluid content with the piston means juxtaposed to the head structure, or in a sterile fluid-containing condition so that sterile gaseous medium in the sealed barrel chamber may be pumped into the multi-dose supply container at the time the barrel chamber is loaded with parenteral liquid.

If it is desirable to mold the piston cap 82 and piston stem 76 as an integral unit from a somewhat elastic plastic, such as polyethylene, it may be found that the diametrically-opposed legs 87, 87 of the piston cap are more flexible than that desired to assure that the latter will remain, during handling and sterilizing, securely mounted on the rear end of the barrel 50, such as in the position of FIG. 1. The piston cap legs, such as 187, 187 of FIG. 13, may be stiffened to avoid such accidental disengagement, such as by thickening the stock thereof, which may be accomplished by providing longitudinally-extending exterior stiffening ribs 98, 98, as proposed in FIG. 13. Such expedient of stiffening the piston cap legs 187, 187 may be particularly desirable if the tips 86, 86 of such legs are narrowed or rounded off to provide camming surfaces for camming engagement of the finger wings 89, 89 in forward thrust of the plunger assembly 75, so as to prevent the finger wings from stopping the piston action before complete expulsion of the chamber contents; and, if desired, such piston cap legs may be extended so that when the plunger assembly is in its fully retracted or rearmost position portions thereof will always remain interdigitated with respect to the finger wings.

Figure 14:
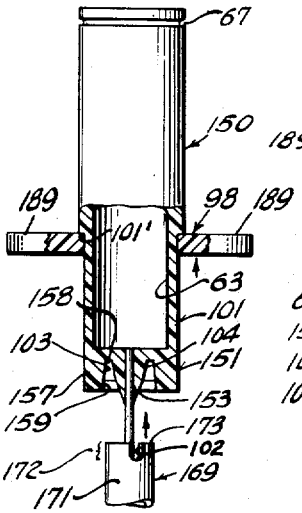
FIG. 14 is a side elevational view, with parts broken away and in section, of a modified form of barrel and head end protective cap structure which may be employed to advantage in the hypodermic syringe structure illustrated in FIGS. 1 to 12 inclusive.
Figure 15:
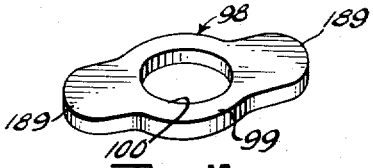
FIG. 15 is a perspective view of finger wing structure embodied in the syringe assembly illustrated in FIG. 14.

As illustrated in FIGS. 14 to 17 incl., the finger wings may be separately mounted to the barrel 150 rather than being molded integral therewith. As illustrated in FIGS. 14 and 15, the finger wings may be provided by a separate piece 98 having an apertured mid-portion 99 provided with a through hole 100 which slidably receives a stepped head section 101 of the barrel 150 to abut against a circular shoulder 101' provided by the barrel stepping for locating the finger wings 189, 189 flanking the mid-section 99 in the desired position along the barrel.

Figure 16:
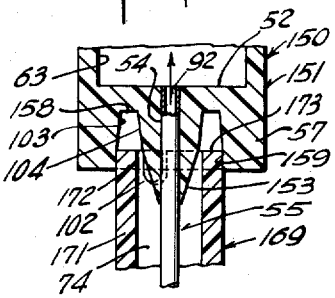
FIG. 16 is an enlarged axial section with parts broken away of barrel head end and associated cap structures of the embodiment of FIG. 14, showing the valved passage for sterilizing gases in open condition.
Figure 17:
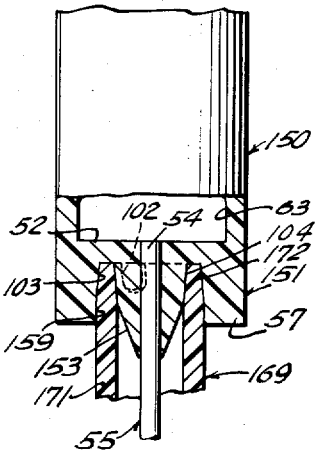
FIG. 17 is a side elevational view substantially to the scale of FIG. 16, with parts broken away and in section, of the structure shown in FIGS. 14 and 16, illustrating closure of the valved passage for sterilizing gases.

Also as indicated in FIGS. 14 to 17 incl., the valved sterilizing-fluid passage at the front cap means may be provided in a modified form. As here illustrated, the needle-protective cap 169 may have a cylindrical side wall 171, the skirt edge zone 172 of which is provided with a longitudinally-extending notch 102. The head structure 151 of the barrel 150 may have a forwardly-extending coaxial flange 157 defined by an outer cylindrical inner wall section 159 and an inner frusto-conical inner wall section 103 merged therewith. The needle boss 153 may have an exterior frusto-conical surface 104 at its root which defines with the surface 103 a tapered annular groove bottom 158 into which the free edge 173 of the needle-protective cap 169 is to be wedged in the valve closing position. As illustrated in FIG. 16, in the initial assembly of the parts of the hypodermic syringe device of the FIGS. 14 to 17 inclusive embodiment a relatively short zone of the side wall free edge 172 of the needle protective cap 169 is telescoped into the cylindrical section 159 of the inner surface of the head flange 157 for holding the parts together temporarily and with a portion of the notch 102 uncovered or open. Thus, the space 74 within the cap 169 communicates directly at the cap with the atmosphere surrounding the syringe assembly through the uncovered portion of notch 102, as indicated in FIG. 16. After the hypodermic syringe assembly of the FIGS. 14 to 17 inclusive embodiment has been suitably sterilized, such as in the manner indicated above, the needle-protective cap 169 will be pushed forward to wedge its edge zone 172 within the tapered annular groove bottom 158, as indicated in FIG. 17, thereby securely closing off in a fluid-tight manner the sterilizing-fluid passage provided at the cap by the notch 102.

Figure 18:
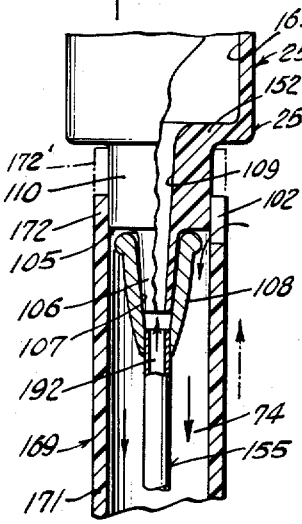
FIG. 18 is a side elevational view, with parts broken away and in section, of a modified form of barrel head end structure, needle mount and protective cap means, illustrating in full lines the relative positions of parts when the valved passage provided thereby is in open condition and in dot-dash lines the relative positions thereof when the valved passage is closed.

A further embodiment of the invention is illustrated in FIG. 18 and as there shown the head structure 251 of the barrel 250 may be provided with a stepped axially-extending neck 105 having a tapered tip 106 which may be wedgably telescoped into a tapered socket 107 in hub 108 of a removable needle 155 to communicate the needle bore 192 with neck bore 109 which leads to barrel chamber 163. The needle-protective cap 169 may be similar in structure to that proposed in the FIGS. 14 to 17 inclusive embodiment, having a free edge zone 172 of the skirt or cylindrical side wall 171 provided with notch 102 to serve as a valved sterilizing-fluid passage at the cap. The edge zone 172 of the cap telescopically receives a substantially cylindrical enlargement 110 of the stepped neck 105 and when the cap 169 is in the position illustrated in full lines in FIG. 18 a portion of the notch 102 remains uncovered to permit fluid to pass therethrough from the atmosphere surrounding the assembly to the space 74 within the cap. After the assembly is sterilized in a manner such as that indicated above, the cap 169 will then be pushed forward to the dot-dash position indicated at 172' in FIG. 18 so that the notch 102 and fluid passage provided thereby is wholly closed by complete lap of the circular land or enlargement 110 of the neck.

If it is desirable or demanded that all exterior surfaces of neck 106 in FIG. 18 which are to be socketed into and lapped by the internal wall of a needle hub socket, such as 107 of the hub 108, of a removable needle unit, such as 155, be sterilized by sterilizing fluid, this may be readily accomplished by having the needle unit initially loosely disposed or housed within the front protective cover, such as 169. The front protective cover or cap 169 may be of such length with respect to the length of the needle unit so that when the cap is pushed to its rearmost position for closing the sterilizing fluid passage leading to the exterior thereof, it will carry with it rearwardly the needle unit to socket the hub 108 of the latter over the container neck 106 to a jamming secure position. For this purpose, the neck 106, needle unit 155 and its hub 108 may be of such relative dimensions and lengths that in the initial position with the needle tip in the vicinity of the closed outer front end of the front protective cap 169, the very tip of the neck 106 is loosely disposed within the mouth at the back end of the hub socket 107, so as to guide the subsequent telescopic jamming of the neck within the hub socket upon rearward thrust of the front protective cap.

Figure 19:
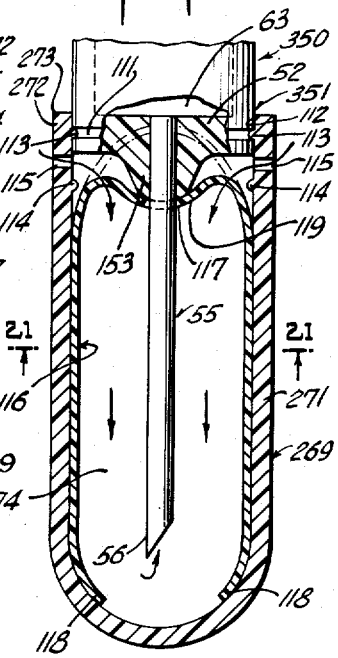
FIG. 19 is a view similar to FIG. 18, illustrating still another form of hypodermic syringe structure of the present invention with the valved passage open and featuring a resilient guide strip which upon withdrawal of the protective cap prevents contamination of the injective tip of an injection needle included in the assembly.
Figure 21:
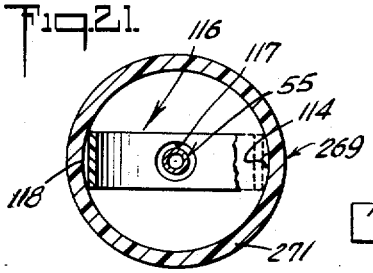
FIG. 21 is a sectional view, with parts broken away, taken substantially on line 21—21 of FIG. 19.
Figure 20:
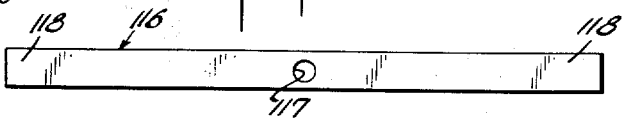
FIG. 20 is a plan view of the protective resilient guide strip illustrated in FIG. 19 in flat initial form before being doubled back for insertion in the protective cap.

In embodiments of the present invention it may be important to sterilize all surfaces of the cap which may be brought, even accidentally, into contact with any portion of the needle which is to be inserted into a patient's flesh so that there can be no possibility of contamination of the insertable portion of the needle by the person who is to administer the injection when he removes the needle protective cap from the sterilized assembly for loading and subsequent injective use. For example, any zone of the inner wall of the cap, such as that adjacent the free edge thereof, which may have lapped barrel structure or head structure of the latter during the sterilizing process may not have during the latter become completely sterilized and when the cap is withdrawn, the latter may be dragged against the tip of the needle to tend to contaminate it. As proposed in FIGS. 19 to 22 inclusive, such possibility of contamination may be eliminated with assurance by mounting a needle guide means within the needle-protective cap with the guide having its parts, which may drag against the needle during cap withdrawal, thoroughly sterilized and preventing contact between the needle and any portion of the cap which may not have become thoroughly sterilized during the sterilizing process. For example, the syringe barrel 350 may have a head structure 351 provided with an external annular groove 111 and with the adjacent surfaces of the head structure being substantially cylindrical for sliding lap with cylindrical inner surface 112 of edge zone 272 of a needle-protective cap 269. The needle-protective cap 269 may have two sets of diametrically-opposed or a plurality of radially-spaced nibs 113—113 and 114—114 with the former set of nibs being located nearest the free edge 273 of the cap. When the cap 269 has its cylindrical side wall 271 telescopically assembled to the barrel 350 in its initial sterilizing position as illustrated in FIG. 19, the set of nibs 113—113 snap into the barrel annular groove 111 securely to hold the parts together. In such position a plurality of apertures 115—115 extending through the side wall 271 near the free edge of the cap 269 or edge zone 272 thereof remain uncovered and open to provide communication directly between the atmosphere exterior of the barrel and cap and the space 74 within the latter so that sterilizing gaseous medium may flow through such cap side holes, the space within the cap and the bore of needle 55 to the barrel chamber 63. In the FIGS. 19 to 22 inclusive embodiment, needle guide means 116 is provided which may be in the form of an elongated strip of semi-rigid elastic material, such as a springy strip of semi-rigid plastic, e.g. Vinylite, etc. Such needle guide strip 116 has a medial needle-receiving aperture 117 to permit it to be slipped loosely down over the needle 55, and its opposite ends 118, 118 are to be folded back or lapped toward each other, as indicated partially in dot-dash lines in FIG. 19. The lapped back ends 118, 118 of the needle guide strip 116 will then be received within the cylindrical side wall 271 of cap 269 as it is telescoped forward to lap of the barrel head 351 and in doing so a reverse band, such as that indicated at 119, may be formed in the medial portion the the strip adjacent the needle-receptive hole 117.

Figure 22:
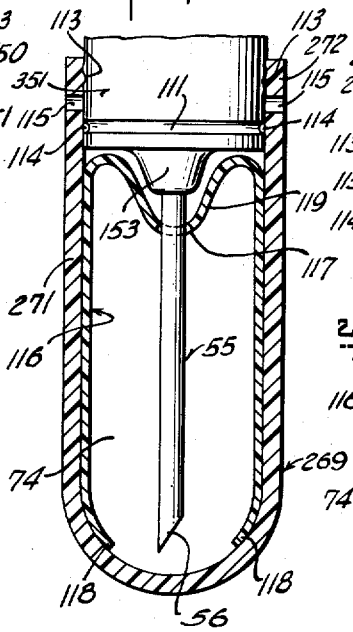
FIG. 22 is a view similar to FIG. 19, illustrating manipulation of the cap to close the valved passage.

In operation of the embodiment illustrated in FIGS. 19 to 22 inclusive, after the assembly has been sterilized with the cap 269 in an initial valve-open position relative to the barrel 350, as illustrated in FIG. 19, the cap will be telescoped farther back upon the barrel head structure 351, such as to the valve-closing position illustrated in FIG. 22, until the second set of internal nibs 114—114 snap into the barrel head groove 111 to hold the parts in their relative positions of closure of the valved sterilizing fluid passage provided by the side holes 115—115. This increases the lap by the edge zone 272 of the cap relative to the substantially cylindrical barrel head structure 351 to close off the passage holes 115—115 in a substantially fluid-tight manner. The sets of nibs 113—113 and 114—114 do not interfere with such telescopic movement of the cap 269 relative to the barrel head 351 if the cap is molded from material having some elasticity so that the small localized nibs will readily flatten out when pressed against barrel structure and for this purpose the cap and its nibs may be molded integrally from elastic plastic, such as polyethylene. In telescoping the needle-protective cap 269 from the initial valve-open position illustrated in FIG. 19 to the valve-closing position illustrated in FIG. 22, the foreshortening of the space 74 within the cap causes some accommodating distortion of the needle guide strip 116, such as an exaggeration of the reverse bend 119 in the mid-portion of the strip adjacent the needle hole 117, as illustrated in FIG. 22.

Assume sterilization of the hypodermic syringe assembly of the FIGS. 19 to 22 inclusive embodiment in a manner such as that described above when the parts are in their relative positions illustrated in FIG. 19 and subsequent closing of the valved sterilizing fluid passage provided by the cap side holes 115—115 by inward thrust of the cap 269 to the position of FIG. 22 and distribution of the sterilized assembly to a user. The user, in preparing to load the syringe barrel chamber 63 with the body of parenteral liquid, will withdraw the cap 269 off from the barrel head structure 351 and the needle 55. The zone of the inner wall of the cap free edge 272, which lapped the exterior surface of the head structure 351 in the position of FIG. 19 during sterilization, perhaps would not be effectively sterilized. Thus, in withdrawing the cap 269 from off of the needle 155 the user might accidentally drag such contaminated inner zone of the cap against the needle tip 56 in the absence of the needle guide strip 116. However, with the needle guide strip 116 present in the cap 269 withdrawal of the cap permits the reverse bend 119 of the medial portion of the strip 116 to relax and reverse to an arched position similar to that indicated in dot-dash lines in FIG. 19, and upon further withdrawal the needle 55 slides out of the central hole 117 of the guide strip and is prevented from moving laterally or radially in any direction thus keeping its tip 56 out of contact with the contaminated zone of the inner wall of the cap skirt.

The embodiment illustrated in FIGS. 23 to 27 incl. is preferred since it has proven by tests to represent a highly desirable form for marketing the invention. In this embodiment the complete assembly, referenced 400, includes a barrel structure 450 which may be suitably molded from any suitable material, and preferably may be a plastic of a composition substantially non-contaminable of parenteral liquid to be loaded thereinto and injectively discharged therefrom. For example, barrel 450 may be molded from polyethylene which is somewhat elastic when in thin section. Barrel means 450 preferably comprises a proximal or head end structure 451, including a head cross wall 452 carrying an outwardly-projecting boss or neck 453 through which is fixed the distal or back end 454 of an injective cannula or needle 455 having its tip 456 sharpened for facilitating subcutaneous insertion. The barrel head end structure 451 also includes a forwardly-extending cylindrical flange 457, arranged concentric with the needle-anchoring boss 453 to provide therebetween an annular groove 458, and terminating in a forward circular edge 459. The back face of cross wall 452 preferably is concaved, as indicated at 460, and provided with a recess 461 into which needle back end 454 reaches, as shown in FIGS. 23 and 25. The barrel structure 450 preferably has a cylindrical side wall 462 which defines a cylindrical bore 463 closed off at the front end by head structure cross wall 452 and with which the bore of cannula or needle 455 communicates in recess 461. Thus, the cannula or needle bore constitutes the liquid outlet passage for the parenteral liquid chamber defined by the cylindrical side wall 462 and the head structure cross wall 452. Near the distal or back end of the barrel structure 450 bore 463 preferably is provided with an internal constriction or circular rib 464 to serve as a plunger or piston plug retraction limiting stop, as is more fully explained hereinafter. Rearwardly of the stop rib 464 the barrel bore 463 preferably is flared at 465, as is best seen in FIG. 27, to reduce the barrel wall thickness at the distal end, and counterboring may be employed for this purpose, if desired. Such flaring at 465 of the barrel bore 463 provides the rear zone 466 of the barrel cylindrical wall 462 with a substantially thinner wall which, by virtue of being thinner, is somewhat more flexible and elastic. The greatest elasticity of the barrel wall may be provided by this means at its distal or rear edge 468 which forms circumambient lateral back end structure defining an open chamber back end.

An elongated thimble-like cap means or capsule structure 469 is provided for housing protectively the needle 455, and preferably has a nose or front end 470, a longitudinal side wall 471, and a cylindrical distal or rear end 472 which snugly fits or telescopes into the annular groove 458 within the circular flange 457. The protective cap 469 may be molded from any suitable material, such as plastic, and may be substantially rigid when formed of more brittle plastic material, such as polystyrene, or if desired may have some elasticity if molded from a more elastic plastic material, such as polyethylene. Frictional fit retains the cylindrical rear end 472 of the cap 469 within annular flange 457 in the position illustrated in FIGS. 23 and 25. Preferably, the external diameter of cap distal end 472 is slightly greater than the internal diameter of annular flange 457, as will be seen from FIGS. 23, 25 and 26, and the latter will have sufficient elasticity to swell out as shown when the cap distal end is jammed thereinto to assure a fluid-tight seal at that point. As indicated in FIG. 26, the internal diameter of the distal end 472 of the cap 469 may be approximately equal to the external diameter of barrel neck or boss 453. Such a a fluid-tight seal may be assured where the cap 469 is formed of somewhat elastic material, such as polyethylene, with provision of such relative diameters of the interfitting telescoped parts, or by making the external diameter of the neck 453 slightly greater than the internal diameter of the cap distal end 472 and the external diameter of the latter about equal to the internal diameter of the annular flange 457. In the latter case, forcing of the cap distal end 472 back over the neck 453 swells out the former which in turn swells out the annular flange 457 in the telescopic interfitting mount of the cap 469 to the barrel head end 451, there to assure the desired fluid-tight seal. The cap 469 may have an annular laterally-extending flange 473 forward of the cylindrical distal end 472 against which the front edge 459 of annular head flange 457 may be jammed in the telescopic interfitting mount of the cap on the barrel head end 451, which may also contribute thereat to the effectiveness of the isolation of the space 474 internally of the cap from airborne bacteria in the surrounding atmosphere. Provision for passage of sterilizing fluid to the interior of the needle-protective cap 469 will be explained later.

Plunger means 475 of the syringe assembly illustrated in FIGS. 23, 25 and 27 may include suitable piston structure 476, preferably in the form of an elongated hollow shaft or stem having an externally-threaded head end 477 threadably received or mounted within an internally-threaded socket 478 in the back end of a piston plug 479 which may be molded from suitable elastic material, such as rubber or the like. The back or distal end of piston shaft or stem 476 at its root 480 preferably is made or molded integral with an enlarged plugging element 481 which may be substantially cylindrical in shape, as shown, and of such dimensions as to wedge into the flared zone 465 of the open back end of the barrel bore 463 for secure and sealing closure thereof. The plugging element 481 and the piston shaft 476 are housed coaxially within elongated rear cap means or hood 482 which may be molded integral therewith, the hood providing a housing skirt for the piston structure. Preferably the hood 482 is provided with a substantially cylindrical bore 483 which may be only slightly greater in diameter than the outside diameter of barrel wall 462 so as to telescope rather closely about the latter with a relatively narrow annular gap therebetween to minimize possibility of entry of contaminable material therethrough to the open back end of the barrel bore 463. Hood bore 483 defines with the annular land provided by the plugging element 81 an annular groove 484 into which the rear edge 468 of the barrel may be wedged for enhancing the sealing of the rear end of the barrel chamber or bore 463. The plunger means or assembly 475 comprising piston shaft 476, plugging element 481 and rear cap means 482 may be molded integral from any suitable material, such as rigid, semi-rigid, or somewhat elastic plastic, e.g., polystyrene or polyethylene.

The hood 482 is of such length as to assure at least some telescopic lap of the barrel wall 463 in the back end zone 466 by its front end 485 when the plunger means is retracted to its stop position illustrated in FIG. 23 and as determined by the internal stop or abutment means, such as rib 464. This will assure minimization of entry of contaminable material to the piston shaft 476 and into the barrel bore 463 in all mounted positions of the piston means 475, as will be emphasized further later. Preferably, the piston shaft 476 carries outside abutment means, such as an annular rib 486, in the vicinity of the base of the externally-threaded head end 477 to abut the internal barrel abutment means or rib 464 upon retraction of the plunger means 475 to determine the stop position of the latter. No difficulty in assembling the plunger means 475 with the barrel 450 is caused by this structure since at least the latter is of elastic material to permit the internal rib 464 thereof to be swelled and/or somewhat flattened for allowing the piston rib 486 to be thrust forward therepast in telescoping the piston shaft initially into the cylindrical barrel wall 463. Structure of the piston plug 479 may be relied upon to serve as such cooperative stop abutment means. For example, the piston plug may conventionally carry a plurality of axially-spaced outside annular ribs 487—487 and the rearward one thereof may be moved back, with retraction of the plunger means 475, to abutment of the internal barrel rib 464 to determine the stop position of the plunger means relative to the barrel 450. Of course, the internal barrel abutment means may be in other forms, such as one or more inwardly-extending projections or nibs, to serve a like purpose.

In order to facilitate manual grasp and manipulation of the hypodermic syringe device 450 is provided with suitable finger grasps, such as a pair of diametrically-opposed, laterally-extending finger wings 489, 489 which are located at points forward of the front end 485 of hood 482 when the plunger means 475 is pushed completely forward to the barrel chamber zero capacity or fully expelled position, shown in FIG. 25, with the shaped nose 488 of piston plug 479 substantially juxtaposed to shaped back wall 460 of the head structure cross wall 452.

Various types of index or scale means may be provided cooperatively on the barrel 450 and the rear cap 482 to guide the amount of load or quantity of parenteral liquid drawn into the barrel bore or chamber 463 retraction of the plunger assembly 475. Such index or scale means may comprise a series of marks (not shown) imprinted the exterior surface of the barrel wall 462, with each suitably identified with volume indicia, such as "0 cc.," "½ cc.," "1 cc.," "1½ cc.," and "2 cc." When the tip of the piston plug nose 488 is brought to substantial alignment with one of these volume marks the volume of the barrel chamber 463 is substantially that indicated by this volume mark on the barrel wall 462, and this may be readily determined by observation when the barrel is molded from transparent or "see-through" material, such as relatively clear plastic, or even foggy polyethylene which in relatively thin section can be clearly seen through.

In order to permit flow of sterilizing fluid through the hypodermic syringe assembly illustrated in FIGS. 23 to 27 inclusive, a fluid passage is provided at the needle-protective cap means 469 which is of a form as, after sterilization, to isolate the injective needle 455 and the neck 453 of the barrel 450 from airborne bacteria which likely are present in the surrounding atmosphere or air. Such passage preferably is provided by a small through hole 490 in the nose 470 of the cap 469, this hole preferably being of the order of about 0.015" to 0.020" in diameter, backed by a porous body 491 of sterile material, such as a wad of sterilized cotton wool. In order to hold the porous sterilized body 491 in filtering position in the cap nose 470, the inner cap wall 474, preferably is provided with an internal annular rib 492 past which the cotton wad is jammed into the cap nose. Thus the small hole 490 and porous sterilized body 491 will permit passage of fluid from outside into the interior of the cap, about the injective needle 455 and the front end of the barrel neck 453, and through the needle lumen to the barrel chamber 463. When the assembly is surrounded by bacteria-laden atmosphere the gaseous medium or air may have such free passage, but the airborne bacteria will be blocked out by the sterilized cotton wad 491.

Passage of sterilizing fluid is also permitted at the distal end of the barrel when the piston assembly 475 is in either the retracted position of FIG. 23 or the telescoped forward position of FIG. 25. In the FIG. 23 retracted position, fluid will flow through the small annular space between the external surface of the cylindrical barrel wall 462 in its back or distal end zone 466 and the internal surface of the skirt or hood bore 483, across the distal end edge 468 of the barrel and into the open back end 465 of the barrel bore 463. Due to the elasticity of at least one of the abutment ribs 464 and 486, and the fact that the piston assembly 475 is slidable forward relative to the barrel 450, the fluid can flow between the cooperative abutment ribs 464 and 486 and past the elastic piston plug 479 due to the elasticity of its annular outside ribs 487—487. This flow is attained under conditions of appreciable differential between internal and external pressures, which obtain in standard practices of evacuation and high pressure flow of sterilizing fluids. When the plunger assembly 475 is then thrust forward to the position of FIG. 25, the barrel back edge 468 is jammed into the annular groove 484 to close this back end passage into the barrel, and thus this back end fluid passage is in the form of a manually-manipulable valved passage. Rapid change in the pressure differential, particularly if the latter is to be appreciable, may cause the plunger assembly 475 to travel forward from the FIG. 23 position toward or to the FIG. 25 position relative to the barrel 450 and, of course, in such case, there is free passage of fluid at the internal stop rib 464 and little or no need for subsequent manual telescope or thrust of the plunger assembly to an appreciable extent for minimizing the overall dimensions of the hypodermic syringe assembly for packaging and marketing.

Such sterilizing flow through the back end of the syringe assembly preferably is attained when the parts thereof are in the relative positions illustrated in FIG. 25, i.e., their telescoped positions as the assembly is packaged for marketing. In this condition, the distal end edge 468 of the barrel is jammed into the annular groove 484 with the flared end zone 466 expanded or swelled to ride up over the annular land 481. Even though this may constitute a manually-manipulatable valve at the back end of the assembly, it may also be considered to be an automatic valve operable by differential in pressure. For example, due to the elasticity of the barrel wall and likewise that of the wall of the skirt or hood 482 when the latter is also made of elastic material, such as polyethylene, if the internal pressure in the assembly back of the piston plug 479 is appreciably greater than the surrounding atmosphere, the barrel wall in the back end zone 466 will be swelled out away from face contact with the annular piston shaft root land 481 to permit fluid flow therebetween, and it has been found that if the differential in internal and external pressures be reversed, there will be such an elastic motion of the parts of the back end valve as to permit fluid flow therethrough. It has also been found that such elasticity of parts permits fluid flow under conditions of differential pressures along the side wall of the elastic piston plug 479, particularly when contact between it and the internal surface of the barrel wall 462 is limited to a plurality of axially-spaced line contacts provided when the elastic piston plug ribs 487—487 are employed.

A plurality of such hypodermic syringe assemblies, such as that illustrated in FIG. 25, may, for the purposes of sterilization, be loaded into a closable sterilizing tank. After loading of the sterilizing tank, it is closed and the air therein and in the open syringe assemblies is exhausted to an appreciable degree of evacuation. It is preferred in practice to pull a vacuum of about 737 mm. (29") of mercury in a rapid manner. This quick change in pressure is accompanied by a violent escape of air from each of the syringe assemblies both from the unsealed injective needle protective cap 469, via its hole 490, and from the barrel chamber 463 and all of its surfaces through the automatic elastic valve at the distal end edge 468 of the barrel. Thereafter, suitable sterilizing fluid or gaseous medium, such as formalin, steam or, preferably, ethylene oxide, is led into the closed tank to flow completely through the hypodermic syringe assemblies therein. This flow of sterilizing fluid through the isolating cotton wad 491 aseptically destroys bacteria that may have been entrapped thereby when the air was exhausted from the spaces internally of each syringe assembly and any bacteria which may have existed on the plunger-barrel surfaces.

Thereafter, the closed tank is again evacuated, preferably to a high degree of evacuation such as that employed in exhausting the air, so as to remove the sterilizing gas from the voids in the syringe assemblies, and then sterile air is released into the tank to fill these voids. Thus when the telescoped syringe assemblies are removed from the sterilizing tank, the internal voids of each are loaded with sterile air, such voids including the interior space of the injective needle protective cap 469 back of the filtering cotton wad 491, the needle lumen, the small cavity in the syringe barrel between the head cross wall 452 and the piston plug 479, the annular spaces intervening the piston plug ribs 487—487 and the internal wall 463 of the barrel chamber, and the chamber proper between the piston plug and the distal end valve at the barrel back edge 468. The sterile air is trapped in the syringe barrel chambers to remain therein as the syringe assemblies are packed in sterile envelopes and until the latter are opened and the syringes manipulated. Hospital trials have shown that such sterilized syringe assemblies meet the aseptical requirements of the medical profession.

In use and operation of such a sterilized hypodermic syringe assembly, such as that illustrated in FIG. 25, the physican, nurse or other person who is to administer to a patient an injection of parenteral liquid will remove the syringe from its protective envelope and then retract the piston assembly 475 to the stop position illustrated in FIG. 23, drawing atmospheric air into the barrel chamber 463 via the needle lumen, the space in its protective cap 469, the porous sterilized cotton wad 491 and the inlet hole 490 in the cap nose. The air drawn in through the cap nose hole 490 is filtered through the sterilized cotton wad 491 to free any airborne bacteria therefrom and, simultaneously, the sterile air in the barrel chamber 463 behind the piston plug 479 is forced back out through the back end valve at the distal end edge 468, which is manually opened by this plunger retraction. This discharge of sterile air from the barrel chamber 463 sweeps away atmospheric air which may have filtered into the space between the inner hood wall 483 and the external surface of the barrel wall 462 after removal of the protective envelope. The operator then removes the protective cap 469 and thrusts the needle tip 456 through the pierceable seal of a suitable multi-dose container carrying the parental liquid and discharges thereinto the air which had been drawn into the barrel chamber 463 by retraction of the plunger asembly 475, temporarily to develop an elevated pressure therein which will assist in subsequent accurate filling of the barrel chamber with the parental liquid. The needle tip 456 is then immersed in the body of parenteral liquid and the plunger assembly 475 retracted to load the barrel chamber 463 with the desired quantity of the liquid, with the pressure imposed on the liquid by the air which had been forced into the container assuring that the liquid will be transferred readily through the needle lumen to the barrel chamber.

During this manipulation of the syringe assembly by the operator, contact of the piston shaft 476 by the operator's fingers is prevented since the hood 482 maintains, in all positions, telescopic lap with the barrel wall 462, so as to avoid any possibility of transfer of any contamination to the piston shaft and the distal end of the barrel which might be carried down into the barrel chamber with manipulative forward thrust of the plunger assembly there to transfer contaminating bacteria to the chamber walls by diffusion or actual flow. This is important since, if contaminating bacteria had been so transferred to the internal chamber wall, manipulative withdrawal of the plunger assembly would permit the piston plug, in wiping the contaminated barrel wall, possibly to transfer some of the contaminating bacteria to the chamber space ahead of the piston plug for subsequent admixture with the parenteral liquid drawn thereinto for hypodermic injection.

An embodiment of the hypodermic syringe assembly, illustrated in FIGS. 23 to 27 inclusive as produced for market, has a barrel chamber capacity of 2½ ccs. with a diameter of about 0.365″ at the stop rib 464 and a length between the latter and the head wall 452 of about 2″. The outside diameter of the barrel is about 0.450″ and the internal diameter of the flared zone 466 at the distal end edge 468 is about 0.375″. The hood 482 has an internal diameter at its distal end of about 0.455″ and the land 481 there at the root of the piston shaft 476 has an outside diameter of about 0.375″. The needle protective cap 469 has an overall length of about 2½″ and an internal diameter at its distal end 472 of about 0.25″ with the outside diameter of the barrel neck 453 in the annular groove 458 preferably being equal to this internal cap diameter. The outside diameter of the distal end 472 of the cap is about 0.343″ and the internal diameter of the barrel head flange 457 is about 0.34″. The cap passage hole 490 is about 0.016″ in diameter and the length of the cotton wad 491 is about 0.25″. It will thus be seen that fluid passages are provided at the proximal end of the assembly, more particularly at the needle protective cap thereof, by the constantly open passage hole 490 and the filtering porous cotton wad 491 backing the same, and at the distal end of the assembly by the valved passage at the distal end edge 468 of the barrel, which is openable either manually or automatically by a pressure differential. Thus the voids within the syringe assembly are isolated from airborne bacteria in the surrounding atmosphere by the isolating filtering passage at the needle-protective front cap or proximal end, and by the valved passage at the distal end, with the front cap securely sealed in a fluid-type manner to the barrel head by the tight telescopic mount thereat while being slidably removable. In the embodiment produced for market, all parts of the syringe except the cotton wool filtering wad, the sterile needle and the rubber piston plug are molded from polyethylene.

It is to be understood that embodiments of the hypodermic syringe of the present invention may be provided in forms which do not require injective needles, or in which the injective needles are supplied separately to be removably fitted to the barrel heads such as is the case of needles having socketed hubs which frictionally receive tapered outlet necks extending from the barrel heads with the neck bores communicating with the barrel chambers to serve as the outlet passages for the latter. It is obvious that embodiments of the invention may employ plunger means in which the piston stem and piston head are made integral with each other, being molded in one piece, if desired, from suitable elastic material.

When plastic materials are employed which can withstand considerable heat without undue or distortional softening sterilization of a closable embodiment of the invention may be accomplished by heat radiation and/or conduction with the construction or assembly in closed condition so that after such heat sterilization the closed condition will maintain until use the sterile condition of the sterilized closed assembly. Thus, for example, the assembly of FIGS. 1 to 12 incl. may be so sterilized by heat when the assembly is in the closed condition of FIGS. 6 and 7. In the FIGS. 14 to 17 incl. embodiment such heat sterilization will be accomplished with the parts in the relative closed positions of FIG. 17. Heat sterilization of the FIG. 18 embodiment may be effected with the protective cap 169 in the dot-dash position indicated at 172′. Since heat sterilization effectively sterilizes lapped surfaces the embodiment of FIGS. 19 to 22 inclusive may be heat sterilized when in the closed FIG. 22 condition, and in such case needle-guiding means, such as strip 116, is not needed since all surfaces of cap 269 are freed from contamination and the interior surfaces remain sterile. The FIGS. 23 to 27 inclusive embodiment will be heat sterilized in the closed condition of FIG. 25.

It will thus be seen that in the embodiment of FIGS. 1 to 12 inclusive at least the cap 69 is of a structure to provide thereat a front end sterilizing-fluid passage in that the cap skirt zone 72 has an outer cylindrical surface, slidably lapped against the inner wall of axial head flange 57 defining cap-receiving annular groove 58, which is radially-spaced from flange wall portions at longitudinal grooves 60—60 in the axial flange, and an inner circular edge 73 axially-spaced outward of the inner ends of these longitudinal grooves in the outward position of the cap shown in FIG. 1. Actually this front end flow passage is provided by the cooperative shaping of the cap skirt zone 72 and head flange 57 which is dependent for provision at least upon the structure of the cap. In the FIGS. 14 to 17 inclusive embodiment at least cap 169 is of a structure for a like purpose, its skirt zone 172 being provided with passage notch 102 the edges of which together with the outer end of head flange 57 at the locality of this cap notch define the front end flow passage in the valve-open position of FIG. 16. Also, in the FIG. 18 embodiment this obtains since the edges of cap notch 102 and the outer end of the cylindrical portion or enlargement 110 of stepped barrel neck 105 together define the front end flow passage in the full line valve-open position of FIG. 18. In the FIGS. 19 to 22 inclusive embodiment the front end flow passage is defined collectively by holes 115—115 in skirt zone 272 of cap 269 when the latter is in its forward valve-open position of FIG. 19, and thus at least this cap is of a structure providing thereat the front end flow passage. Likewise, in the FIGS. 23 to 27 inclusive embodiment the hole 490 in the cap tip 470 provides the front end flow passage, so that at least cap 469 is also of a structure to provide the front end flow passage.

In all embodiments illustrated in the drawings one of the cap and head means has blocking means preventing flow of bacteria-laden air through the front end sterilizing-fluid flow passages into the interiors of the sterilized assemblies. In the FIGS. 1 to 12 embodiment this blocking means are closed valves, each valve being the portion of the terminal margin of the cap skirt zone 72 which laps against the inner wall of the axial flange 57 inward of the bottom end of each longitudinal groove 50 in the closed position of FIG. 6. The FIGS. 14 to 17 inclusive construction provides this blocking means in the form of the portion of the head means axial flange 57 against which the portions of cap skirt zone 172 adjacent the passage notch 102 lap to close off this passage notch in the closed position of FIG. 17. In the FIG. 18 construction that portion of the cylindrical surface of neck enlargement 110 which is opposed to front end flow passage notch 102 and laps against flanking portions of the inner wall of cap skirt zone 172 in the dot-dash closed position of FIG. 18 constitutes the blocking means for this passage, and neck enlargement 110 constitutes part of head means 251. The FIGS. 19 to 22 inclusive construction locates the blocking means on the head means 351 in the vicinity of the head cross wall 52 as the portions of the outside surface of barrel 350 that are lapped against those portions of the inner wall of cap skirt zone 272 which flank the front end passage holes 115—115 in the FIG. 22 closed position. The cap means 469 of the syringe assembly 400 shown in FIGS. 23 to 27 inclusive has the blocking means in the form of sterile cotton wad 491 which is held in the cap tip 470 by internal rib 492 behind the front end flow passage provided by hole 490, so as to prevent flow of bacteria-laden air through this passage into the sterilized interior of the assembly. Although gaseous medium may flow through front end flow passage hole 490 under the influence of a differential in pressure of atmospheres inside and outside of the assembly 400 the cotton wad filter 491 prevents ingress of airborne bacteria, the gaseous carrier of bacteria-laden air may go through but the carried bacteria cannot and thus flow of bacteria-laden air through the front end flow passage into the assembly is blocked.

The blocking means for the back end flow passage of the illustrated embodiments is provided as cooperating inter-engaging means of the barrel means and the plunger sub-assembly (including the plunger stem, the surrounding hood and the distal or back end connection thereof), in the form of a valve structure at the root of the plunger stem. However, such blocking means may be located elsewhere along the back end flow passage, such as between the hood and the exterior of the barrel. For example, the barrel wall may carry an external annular flange as a base on which the finger grasps or wings are mounted, or as a separate element located therebehind, against which the free front edge of the hood is jammed or with which it is interfitted.

It will thus be seen that the objects set forth above, among those made apparent from the preceding description, are efficiently attained and, since certain changes may be made in the above constructions without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Having described my invention, what I claim as new and desire to secure by Letters Patent is:

1. A closed sterilized hypodermic syringe assembly comprising, in combination; hollow barrel means having head means closing off one end thereof and together defining a chamber for containing parenteral liquid, the back end of said barrel means terminating in circumambient structure defining an open chamber back end, said head means having a liquid outlet passage communicating with said chamber for injective discharge of liquid contents; removable protective cap means having a back end supported by said head means and isolating the outlet passage from airborne bacteria in the surrounding atmosphere exterior of said barrel and cap means, at least said cap mean being of a structure to provide thereat a front end sterilizing-fluid flow passage leading from the surrounding atmosphere directly to the space therein while said cap means remains supported by said head means to permit pressure flow of sterilizing fluid into and out of the cap means and about structure housed in said cap means via the liquid outlet passage and this sterilizing-fluid passage, one of said cap and head means having blocking means preventing flow of bacteria-laden air through the front end sterilizing-fluid flow passage into the interior of the sterilized assembly; and plunger sub-assembly means including piston means slidably mounted in a forward position in said chamber for drawing fluid thereinto upon retraction to a rearward position and expelling fluid therefrom upon forward thrust to its forward position, elongated plunger stem means extending through the open back end of said chamber and carrying said piston means on its front end, and an elongated hood having an open front end with its back end being closed and carried by the back end of said plunger stem means, said hood being in a forward position and surrounding a major portion of said stem means with an annular space defined therebetween into which the back end of said barrel means is telescoped with a rear portion of said barrel means protectively housed by overlap thereby, said housed barrel portion and said plunger sub-assembly means being relatively shaped to provide therebetween a back end sterilizing-fluid flow passage leading from surrounding atmosphere at the front end of said hood between the latter and said housed barrel portion to the open back end of the latter for communication to said chamber when said plunger sub-assembly means is retracted to a rearward position with maintenance of connection thereof to said barrel means, said piston means in such rearward position permitting pressure flow therepast of sterilizing fluid into and out of said chamber, said plunger sub-assembly in its forward position and said barrel means having interengaging means serving as blocking means cooperatively closing off the back end flow passage to prevent flow therethrough of bacteria-laden air from surrounding atmosphere into the sterilized assembly.

2. The sterilized hypodermic syringe assembly as defined in claim 1 characterized by the blocking means for the back end flow passage being in the form of valve means having cooperating interengaged elements at the back end of said plunger stem means and the back end of said barrel means.

3. The sterilized hypodermic syringe assembly as defined in claim 2 characterized by said interengaged valve elements being the circumambient back end structure of said barrel means and a plugging element intervening the back ends of said stem and hood, said plugging element being jammed into said circumambient back end structure.

4. The sterilized hypodermic syringe assembly as defined in claim 1 characterized by cooperating stop means on said barrel means and said plunger sub-assembly means limiting retraction of the latter to the rearward position with maintenance of a degree of overlap of the free front end of said hood on the back end of said barrel means.

5. The sterilized hypodermic syringe assembly as defined in claim 1 characterized by said cap means back end and said head means being shaped to provide when the former is mounted to the latter the front end sterilizing-fluid flow passage thereat and openable valve means closing this passage as said blocking means.

6. The sterilized hypodermic syringe assembly as defined in claim 5 characterized by structure of said cap means back end and said head means serving as engaged cooperating valve elements with said cap means back end and said head means being movable relative to each other with maintenance of the amount of said cap means to said head means to a position separable of said valve elements for opening the front end flow passage.

7. A sterilizable hypodermic syringe assembly comprising, in combination; an elongated hollow barrel having head structure closing off one end thereof together defining a parenteral liquid chamber with the other end of said barrel terminating in circular lateral back end structure defining an open chamber back end, said head structure having cap support means and an outlet passage communicating with said chamber for injective discharge of contents; a removable protective front cap slidably supported on said cap support means and defining with the latter an internal space communicating with the outlet passage, said cap and support means together closing off said space and outlet passage from communication with the surrounding atmosphere exterior of said barrel and cap with balanced pressures prevailing inside and outside of said assembly and shaped cooperatively to provide therebetween a first sterilizing-fluid flow passage leading from the surrounding atmosphere directly to the space within said cap while said cap remains supported on said cap support means to permit pressure flow of sterilizing fluid into and out of the cap space and about structure housed in said cap via the outlet passage and this sterilizing-fluid flow passage, portions of said cap and support means being so shaped and cooperatively engaged to serve as manipulative valve means selectively operable to open and close said passage upon relative sliding motion; piston means slidable in said barrel chamber for injective discharge of parenteral liquid contents; and back end cap structure slidably carried on and telescopically arranged about said barrel back end protectively covering said lateral back end structure, said piston means being at least partially housed in said back end cap structure in lateral spaced relation thereto, said back end cap structure and said barrel back end being so shaped cooperatively to provide therebetween a second sterilizing-fluid flow passage leading across said lateral back end structure from the surrounding atmosphere directly to the back end of the chamber and thence into the latter with maintenance of connection of said piston means and back end cap structure to said barrel to permit pressure flow of sterilizing fluid into and out of said chamber via the second sterilizing-fluid flow passage, portions of said barrel back end and at least one of said piston means and back end cap structure being so shaped and cooperatively engaged to serve as additional manipulative valve means selectively operable to open and close the second sterilizing-fluid flow passage upon relative sliding motion.

8. A sterilizable hypodermic syringe assembly comprising, in combination; a cylindrical barrel having a bore providing a parenteral liquid chamber and head structure at one end closing off the bore with the other end of said barrel terminating in circumambient lateral back end structure defining an open chamber back end, said head structure having fixed axially therein a hollow injective needle having a through bore providing an outlet passage communicating with said chamber for injective discharge of contents, said head structure also having cap support means; a removable protective cap slidably supported on said cap support means and defining with the latter an internal space communicating with the outlet passage, said cap and support means together isolating said space and needle from air-borne bacteria in the surrounding atmosphere exterior of said barrel and cap; means including at least portions of the structure of said cap defining a first sterilizing-fluid flow passage at said cap communicating the surrounding atmosphere with said chamber via the space within said cap and needle bore while said cap remains supported by said cap support means to permit the pressure flow of sterilizing fluid into and out of the cap space and about and through said needle housed in said cap, the means defining the sterilizing-fluid flow passage having means to prevent ingress of air-borne bacteria in the surrounding atmosphere; elongated piston means slidable in said barrel chamber for injective discharge of parenteral liquid contents; and an elongated back end cap structure having a cylindrical skirt telescoped over and slidably arranged about said barrel back end protectively covering said lateral back end structure, said back end cap structure carrying said piston means coaxially therein in lateral spaced relation with said barrel back end intervening, said barrel back end and at least one of said piston means and back end cap structure being so shaped and cooperatively engaged to close off the back end of said chamber from communication with the surrounding atmosphere with balanced pressures prevailing inside and outside of said assembly, said back end cap structure and the portion of said barrel back end telescoped thereinto being so shaped relative to each other as to provide therebetween a second sterilizing-fluid flow passage leading from the surrounding atmosphere between said barrel and cap skirt and across said lateral back end structure directly to the open back end of said chamber and thence into the latter to permit pressure flow of sterilizing fluid into and out of said chamber via the second flow passage when said back end cap structure and said piston means are retracted relative to said barrel back end to effect disengagement thereof with maintenance of connection of said back end cap structure and said piston means to said barrel.

9. A sterilized hypodermic syringe assembly comprising, in combination; an elongated cylindrical barrel having a sterilized bore and a head structure closing off the front end of the bore together defining a chamber for containing parenteral liquid with the back end of the bore being open when not plugged; a sterilized, hollow injective needle carried by and extending coaxially from said head structure with its bore in communication with said barrel bore; an axially-extending annular flange arranged about said needle and extending forward from said head structure; an elongated, needle-protective, interiorly-sterilized cap telescoped back over said needle and having a free edge zone telescoped with said annular flange closing off said sterilized needle and front end of said barrel bore from air-borne bacteria in the outside atmosphere; a plunger sub-assembly comprising an elongated, cylindrical rear cap having an open front end and a closed back end providing an elongated cylindrical hood telescoped over and slidably mounted in a forward position on said barrel, and an elongated plunger means mounted coaxially in said hood and carried by the closed back end of said rear cap, said plunger means having a sterilized front end thrust forward in said barrel bore to a foremost position adjacent said head structure; flow blocking means carried by said plunger sub-assembly in engagement with structure of said barrel sealing off the back end of said barrel bore from the outside atmosphere; and cooperating stop means carried by said barrel and said plunger sub-assembly limiting retraction of said plunger means in said bore, said hood being of a length sufficient to maintain lapping telescope thereof on said barrel with cooperative engagement of said stop means.

10. A sterilized hypodermic syringe assembly comprising, in combination; an elongated cylindrical barrel having a sterilized bore and a head structure closing off the front end of the bore together defining a chamber for containing parenteral liquid with the back end of the barrel being defined by a circular end edge and structurally open when the bore is not plugged; a sterilized, hollow injective needle carried by and extending longitudinally from the front end of said head structure with its bore in communication with said barrel bore; an elongated, removable, needle-protective front cap telescoped back over said needle and separably supported by said head structure in a manner isolating said sterilized needle from air-borne bacteria in the outside atmosphere; sterilized, fluid-expelling plunger subassembly structure reciprocatively mounted on the back end of said barrel; said plunger sub-assembly structure comprising an elongated piston post coaxially received in said bore and carrying on its front end piston means snugly and slidably fitted in said bore, and an elongated, cylindrical skirt coaxially surrounding said barrel with intervening annular spacing forward of said barrel back end edge, the back end of said skirt being circumferentially mounted to the back end of said post defining therebetween an annular groove into which the back end edge of said barrel is fitted in a fluid-tight manner with balanced pressure prevailing inside and outside of said assembly thereby plugging the barrel bore; and cooperative stop means on said barrel and plunger sub-assembly structure limiting retraction of the latter relative to said barrel, said skirt being of such length as to maintain telescopic lap of said barrel when said plunger structure is retracted to the limit permitted by said stop means.

11. A sterilized hypodermic syringe assembly comprising, in combination; an elongated cylindrical barrel having a sterilized bore and a head structure closing off the front end of the bore together defining a chamber for containing parenteral liquid with the back end of the bore being wide open when free of obstructing piston structure; a sterilized, hollow injective needle carried by and extending coaxially from said head structure with its bore in communication with said barrel bore; an elongated, removable, needle-protective, interiorly-sterilized front cap telescoped back over said needle and separably supported by said head structure in a manner isolating said sterilized needle and the front end of said barrel bore from air-borne bacteria in the outside atmosphere; an elongated, slidable, cylindrical rear cap having an open front end and a closed back end providing an elongated cylindrical hood telescoped over a major portion of said barrel with intervening lateral spacing, the front end of said hood being located in a forward position on said barrel; elongated plunger means mounted coaxially in and carried by the back end of said hood and including sterilized front end piston means thrust forward in said barrel bore to a foremost position adjacent said head structure; and cooperating means carried by said barrel and hood sealing off communication between the back end of said barrel bore and the outside atmosphere surrounding the assembly in this forward position of said hood on said barrel, the back end of said barrel bore being communicated with surrounding atmosphere via the lateral space intervening said hood and barrel upon retraction of said hood and plunger means with maintenance of the telescopic mount of said rear cap on said barrel.

12. A sterilizable hypodermic syringe assembly comprising, in combination, barrel means providing a parenteral liquid chamber and having head means at one end with its other end terminating in circumambient edge means defining an open chamber back end, said head means having an outlet passage communicating with said chamber for injective discharge of contents, removable protective cap means supported by said head means with provision of a flow passage extending from the exterior to the interior of said cap means, fluid flow-permitting filtering means covering said flow passage and isolating the interior of said cap means and outlet passage from airborne bacteria in the surrounding atmosphere exterior of said barrel and cap means, plunger means reciprocatively mounted in said chamber through its open back end, and a plurality of cooperative valve means on said plunger means and said barrel means closing off fluid communication between said chamber and the surrounding atmosphere when said plunger means is in a forward position in said chamber, said valve means being in relative open positions when said plunger means is retracted.

13. A sterilizable hypodermic syringe assembly comprising, in combination, barrel means providing a parenteral liquid chamber and having head means at one end with its other end terminating in circumambient edge means defining an open chamber back end, said head means having an outlet passage communicating with said chamber for injective discharge of contents, removable protective cap means supported by said head means and having a flow passage extending through a wall portion thereof, fluid flow-permitting filtering means in said cap means covering said flow passage and isolating the interior of said cap means and outlet passage from airborne bacteria in the surrounding atmosphere exterior of said barrel and cap means, plunger means reciprocatively mounted in said chamber through its open back end, and a plurality of cooperative valve means on said plunger means and said barrel means closing off fluid communication between said chamber and the surrounding atmosphere when said plunger means is in a forward position in said chamber with balanced pressures prevailing inside and outside of said chamber, the valve means on one of said plunger and barrel means being elastic to permit automatic opening for allowing fluid flow therepast under conditions of appreciable differential in pressures present inside and outside of said chamber.

14. A sterilizable hypodermic syringe assembly comprising, in combination, barrel means providing a parenteral liquid chamber and having head means at one end with its other end terminating in circumambient edge means defining an open chamber back end, said head means having an outlet passage communicating with said chamber for injective discharge of contents, removable protective cap means supported by said head means and having a flow passage extending through a wall portion thereof, fluid flow-permitting filtering means in said cap means covering said flow passage and isolating the interior of said cap means and outlet passage from airborne bacteria in the surrounding atmosphere exterior of said barrel and cap means, plunger means reciprocatively mounted in said chamber through its open back end, stop means cooperatively located on said plunger and barrel means limiting retraction of the former in the latter, and elongated hood means carried by said plunger means with telescopic lap over said barrel means in all positions of said plunger means between its forward position in said chamber and its retracted position as determined by said stop means, said hood and plunger means providing closure means for the open chamber back end when thrust to their forward positions.

15. A sterilizable hypodermic syringe assembly comprising, in combination, barrel means providing a parenteral liquid chamber and having head means at one end with its other end terminating in circumambient edge means defining an open chamber back end, said head means having an outlet passage communicating with said chamber for injective discharge of contents, removable protective cap means supported by said head means and having a flow passage extending through a wall portion thereof, fluid flow-permitting filtering means in said cap means covering said flow passage and isolating the interior of said cap means and outlet passage from airborne bacteria in the surrounding atmosphere exterior of said barrel and cap means, plunger means reciprocatively mounted in said chamber through its open back end, stop means cooperatively located on said plunger and barrel means limiting retraction of the former in the latter, and elongated hood means carried by said plunger means with telescopic lap over said barrel means in all positions of said plunger means between its forward position in said chamber and its retracted position as determined by said stop means, said hood and plunger means providing with said barrel back end edge means an automatic pressure-operable fluid flow valve means with said hood and plunger means thrust to their forward positions, said valve means in the forward positions of said hood and plunger means being closed with balanced pressures prevailing inside and outside of said assembly and openable by a differential in such pressures.

16. A sterilizable hypodermic syringe assembly comprising, in combination, an elongated cylindrical barrel having a bore providing a parenteral liquid chamber defined at one end by a head structure closing off the front end of the bore with the back end of the latter open when not plugged and defined by a circular end edge; a hollow injective needle carried by and extending co-axially from said head structure with the lumen thereof in communication with said chamber; an elongated, needle-protective cap telescoped back over said needle and removably fitted to said head structure in a fluid-tight manner and having a tip extending beyond the free end of said needle provided with a through hole defining a flow passage, said tip carrying internally thereof fluid flow-permitting filtering means covering said flow passage and isolating the interior of said cap and the needle housed therein from airborne bacteria in the surrounding atmosphere exterior of said barrel and cap; plunger means reciprocatively carried by the distal end of said barrel having a piston stem and head carrried by said stem slidably mounted in said bore chamber and an elongated cylindrical hood co-axially arranged about said stem and mounted on the distal end of the latter; stop means cooperatively mounted on said stem and in said barrel limiting retraction of said plunger means to a retracted stop position with the stem head retained in said bore chamber, the free proximal end of said hood having telescopic lap over said barrel in all positions of said plunger means between the forward position of said stem head in said chamber and the retracted stop position thereof; and valve means selectively closing off the back end of said barrel bore including an annular groove defined between the distal ends of said stem and hood into which the distal end edge of said barrel is jammed in fluid-tight manner when said plunger means is thrust forward to its forward position.

17. A sterilizable hypodermic syringe assembly comprising, in combination, an elongated cylindrical barrel having a bore providing a parenteral liquid chamber defined at one end by a head structure closing off the front end of the bore with the back end of the latter open when not plugged and defined by a circular end edge; a hollow injective needle carried by and extending co-axially from said head structure with the lumen thereof in communication with said chamber; an elongated, needle-protective cap telescoped back over said needle and removably fitted to said head structure in a fluid-tight manner and having a tip extending beyond the free end of said needle provided with a through hole defining a flow passage, said tip carrying internally thereof fluid flow-permitting filtering means covering said flow passage and isolating the interior of said cap and the needle housed therein from airborne bacteria in the surrounding atmosphere exterior of said barrel and cap; plunger means reciprocatively carried by the distal end of said barrel having a piston stem and head carried by said stem slidably mounted in said bore chamber and an elongated cylindrical hood co-axially arranged about said stem and mounted on the distal end of the latter; stop means cooperatively mounted on said stem and in said barrel limiting retraction of said plunger means to a retracted stop position with the stem head retained in said bore chamber, the free proximal end of said hood having telescopic lap over said barrel in all positions of said plunger means between the forward position of said stem head in said chamber and the retracted stop position thereof; and valve means closing off the back end of said barrel bore including an annular groove defined between the distal ends of said stem and hood and the distal end edge of said barrel telescoped into said groove, the distal end edge of said barrel being formed of elastic material with the external diameter of the root of said stem defining the inner wall of said groove being greater than the internal diameter of the barrel distal end edge for swelling fit of the latter thereover and with the internal diameter of the hood at its distal end being greater than the external diameter of said barrel distal end edge to permit this swelling fit, said back end valve means being closed when said plunger means is thrust to its forward position with balanced pressure prevailing inside and outside of said chamber and being automatically openable for allowing fluid flow therepast under conditions of appreciable differential in pressures present inside and outside of said chamber.

18. A sterilized hypodermic syringe assembly comprising, in combination, an elongated cylindrical barrel of elastic material having a sterilized bore and a head structure closing off the proximal end of the bore with the distal end of the latter open when not plugged, said barrel carrying on the wall of its bore forward of the distal end thereof inwardly-projecting stop means to define between it and said head structure a chamber for parenteral liquid; a sterilized, hollow injective needle having a free insertable proximal end and a distal end carried by and extending co-axially through said head structure with the lumen thereof in communication with said chamber; an elongated, needle-protective, interiorly-sterilized cap telescoped back over said needle and having a distal end removably fitted to said head structure in a substantially fluid-tight manner, the other end of said cap providing a tip extending forward of the proximal free end of said needle and having a hole extending therethrough providing a flow passage, said tip carrying therein a sterilized wad of porous filtering material covering said flow passage and isolating the interior of said cap and said needle from airborne bacteria in the surrounding atmosphere exterior of said barrel and cap; an elongated, cylindrical hood having an open proximal end telescoped over and slidably mounted about said barrel and a closed distal end; a plunger stem supported by said hood distal end co-axially within said hood and carrying a sterilized piston head reciprocatively mounted in said chamber between said head structure and said stop means; abutment means carried by said stem cooperating with said stop means limiting retraction of said stem and its head in said chamber with the open proximal end of said hood telescoped over and lapping about said barrel in all positions of said piston head in said chamber forward of said stop means; and barrel bore plugging means on the distal end of said stem telescoped into the distal end of said barrel when said piston head is thrust forward to the vicinity of said head structure with the elastic barrel distal end edge swelled out about said plugging means and providing therewith a valve openable by differential in pressures inside and outside of said chamber with said hood at its distal end having an internal diameter appreciably greater than the external diameter of said swelled edge to permit further valve-opening pressure swelling of the latter without appreciable axial motion of said piston head in said chamber.

19. A sterilizable hypodermic syringe assembly comprising, in combination; cylindrical barrel means providing a parenteral liquid chamber and having head structure at one end with its other end terminating in circumambient lateral back end structure defining an open chamber back end, said head structure having fixed axially therein a hollow injective needle having a through bore providing an outlet passage communicating with said chamber for injective discharge of contents, said head structure carrying cap support means; a removable protective cap slidably supported on said cap support means and defining with the latter an internal space communicating with the needle bore outlet passage, said cap and support means together isolating said space and needle from airborne bacteria in the surrounding atmosphere exterior of said barrel and cap, a wall portion of said cap having a through hole providing a first sterilizing-fluid passage communicating the surrounding atmosphere with said chamber via the space within said cap and needle bore to permit pressure flow of sterilizing fluid into and out of the cap space and about and through said needle housed in said cap; flow-permitting filtering means covering said sterilizing-fluid passage to prevent ingress of airborne bacteria in the surrounding atmosphere; elongated piston means slidable in said barrel chamber for injective discharge of parenteral liquid contents; and an elongated hood structure having a cylindrical skirt telescoped over and slidably mounted on said barrel back end, carrying said piston means co-axially therein and protectively covering said lateral barrel back end structure, said hood structure and lateral barrel back end structure together closing off the back end of said chamber from communication with the surrounding atmosphere with balanced pressures prevailing inside and outside of said assembly and cooperatively providing therebetween a second sterilizing-fluid passage leading from the surrounding atmosphere between said barrel and hood skirt and across said lateral barrel back end structure directly to the open back end of said chamber and thence into the latter to permit pressure flow of sterilizing fluid into and out of said chamber via the second passage, portions of said hood structure and said lateral back end structure cooperatively serving as valve means selectively operable to open and close the second passage.

20. A sterilized hypodermic syringe assembly comprising, in combination; an elongated cylindrical barrel having a sterilized bore and a head structure closing off the front end of the bore with the back end of the latter open when not plugged; a sterilized, hollow injective needle having a proximal inserting free end and a distal end carried by and extending co-axially through said head structure with its lumen in communication with said barrel bore; an axially-extending annular flange arranged about said distal end of said needle and extending forward from said head structure; an elongated, needle-protective, interiorly-sterilized cap telescoped back over said needle and having a distal free edge zone telescoped with said annular flange isolating said sterilized needle and front end of said barrel bore from air-borne bacteria in the outside atmosphere, said cap having a proximal tip forward of the proximal free end of said needle provided with a through hole and carrying interiorly thereof a sterilized body of porous filtering material intervening the hole and the proximal free end of said needle; an elongated, cylindrical hood having an open proximal end and a closed distal end telescoped over and slidably mounted in a forward position on said barrel; elongated plunger means mounted co-axially in said hood and including sterilized front end piston means thrust forward in said barrel bore to a foremost position adjacent said head structure; barrel bore plugging means on the back ends of said barrel and plunger means sealing off the back end of said barrel bore from the outside atmosphere; and cooperating stop means in said barrel bore in the vicinity of the back end of the latter and on said plunger means in the vicinity of the front end of the latter limiting retraction of said plunger means in said bore, said hood being of a length sufficient to maintain lapping telescope thereof on said barrel with cooperative engagement of said stop means.

21. A sterilized hypodermic syringe assembly comprising, in combination; an elongated cylindrical barrel of elastic material having a sterilized bore and a head structure closing off the front end of the bore with the back end of the latter structurally open and defined by an elastic end edge; a sterilized, hollow injective needle carried by and extending longitudinally from the front end of said head structure with its bore in communication with said barrel bore; an elongated, removable, needle-protective front cap telescoped back over said needle and separably supported by said head structure in a fluid-tight manner, said cap having a tip provided with a through hole and carrying behind the hole a sterilized wad of flow-permitting filter material isolating said sterilized needle from airborne bacteria in the outside atmosphere; sterilized, fluid-expelling plunger structure reciprocatively mounted in the back end of said barrel bore; said plunger structure comprising an elongated piston post co-axially received in said bore and carrying on its front end piston means snugly and slidably fitted in said bore, and an elongated, cylindrical skirt co-axially surrounding said barrel and post and circumferentially mounted to the back end of the latter together defining therebetween an annular groove into which the elastic back end edge of said barrel is fitted in a fluid-tight manner with balanced pressures prevailing inside and outside of said assembly; and cooperative stop means on said barrel and plunger structure limiting retraction of the latter relative to said barrel, said skirt being of such length as to maintain telescopic lap of said barrel when said plunger structure is retracted to the limit permitted by said stop means.

*22. A sterilizable hypodermic syringe assembly comprising, in combination; cylindrical barrel means providing a parenteral liquid chamber and having head means at one end with its other end terminating in circumambient edge means defining an open chamber back end, said head means having an outlet passage communicating with said chamber for injective discharge of contents; removable protective cap means temporarily supported by said head means with a front end flow passage defined at least in part by structure of one of said cap and head means and communicating with said outlet passage and the outside atmosphere; front end flow passage blocking means for preventing flow of bacteria-laden air through said outlet passage and isolating the interior of said cap means from airborne bacteria in the outside atmosphere; and plunger sub-assembly means including piston means slidably and snugly mounted in a forward position in said chamber for drawing fluid thereinto upon retraction to a rearward position and expelling fluid therefrom upon forward thrust to its forward position, elongated plunger stem means extending through the open back end of said chamber and carrying said piston means on its front end, and an elongated hood having an open front end with its back end being closed and carried by the back end of said plunger stem means, said hood having a fixed cylindrical shape and surrounding a major portion of said stem means with an annular space defined therebetween into which the back end of said barrel means is telescoped, the open front end of said hood having telescopic lap over said barrel in all positions of said plunger sub-assembly between the forward position of said piston means in said chamber and the retracted position thereof, the inside diameter of said hood being slightly greater than the outside diameter of said barrel to define an annular space between the hood and the barrel through which a steriliz-*

*ing gas may pass from the outside atmosphere to the open chamber back end of said barrel.*

*23. A sterilizable hypodermic syringe assembly comprising, in combination; cylindrical barrel means, providing a parenteral liquid chamber and having head means at one end with its other end terminating in circumambient edge means defining an open chamber back end, said head means having an outlet passage communicating with said chamber for injective discharge of contents; removable protective cap means temporarily supported by said head means and covering said outlet passage and isolating it from airborne bacteria in the outside atmosphere; and plunger sub-assembly means including piston means slidably and snugly mounted in a forward position in said chamber for drawing fluid thereinto upon retraction to a rearward position and expelling fluid therefrom upon forward thrust to its forward position, elongated plunger stem means extending through the open back end of said chamber and carrying said piston means on its front end, an elongated hood having an open front end with its back end being closed and carried by the back end of said plunger stem means, said hood having a fixed cylindrical shape and surrounding a major portion of said stem means with an annular space defined therebetween into which the back end of said barrel means is telescoped, the open front end of said hood having telescopic lap over said barrel in all positions of said plunger sub-assembly between the forward position of said piston means in said chamber and the retracted position thereof, the inside diameter of said hood being slightly greater than the outside diameter of said barrel to define an annular space between the hood and the barrel through which a sterilizing gas may pass from the outside atmosphere to the open chamber back end of said barrel, and*

*cooperating sealing portions on said barrel means and said plunger sub-assembly, said sealing portions fitting tightly together and sealing off communication between said open chamber back end and the outside atmosphere only when the plunger sub-assembly is thrust to its forward position.*

References Cited in the file of this patent
or the original patent

UNITED STATES PATENTS

| | | |
|---|---|---|
| 715,290 | Porter | Dec. 9, 1902 |
| 766,121 | Stearns | July 26, 1904 |
| 1,059,493 | Selleck | Apr. 22, 1913 |
| 1,718,592 | Smith | June 25, 1929 |
| 2,263,865 | Bailen | Nov. 25, 1941 |
| 2,375,929 | Lautenschlager | May 15, 1945 |
| 2,453,590 | Poux | Nov. 9, 1948 |
| 2,490,447 | Lockhart | Dec. 6, 1949 |
| 2,524,363 | Smith | Oct. 3, 1950 |
| 2,539,510 | Friden | Jan. 30, 1951 |
| 2,578,814 | Kollsman | Dec. 18, 1951 |
| 2,626,604 | Nadeau | Jan. 27, 1953 |
| 2,646,043 | Hertig-Husler et al. | July 21, 1953 |
| 2,685,878 | Seifert et al. | Aug. 10, 1954 |
| 2,688,965 | Huber | Sept. 14, 1954 |
| 2,700,386 | Ogle | Jan. 25, 1955 |
| 2,715,905 | Ogle | Aug. 23, 1955 |
| 2,727,514 | Lockhart | Dec. 20, 1955 |
| 2,847,996 | Cohen et al. | Aug. 19, 1958 |

FOREIGN PATENTS

| | | |
|---|---|---|
| 167,058 | Germany | Jan. 13, 1906 |
| 887,677 | France | Aug. 16, 1943 |
| 813,433 | Germany | Sept. 13, 1951 |
| 172,332 | Austria | Aug. 25, 1952 |